(12) United States Patent
Koptenko

(10) Patent No.: US 10,627,510 B2
(45) Date of Patent: Apr. 21, 2020

(54) ULTRASOUND BEAMFORMING SYSTEM AND METHOD BASED ON ANALOG RANDOM ACCESS MEMORY ARRAY

(71) Applicant: URSUS MEDICAL, LLC, Wexford, PA (US)

(72) Inventor: Sergei V. Koptenko, Mississauga (CA)

( * ) Notice: Subject to any disclaimer, the term of this patent is extended or adjusted under 35 U.S.C. 154(b) by 243 days.

(21) Appl. No.: 15/594,875

(22) Filed: May 15, 2017

(65) Prior Publication Data
US 2018/0003819 A1     Jan. 4, 2018

Related U.S. Application Data

(63) Continuation of application No. PCT/US2015/060861, filed on Nov. 16, 2015.
(Continued)

(51) Int. Cl.
*G01S 15/89*     (2006.01)
*G01S 7/52*      (2006.01)
(Continued)

(52) U.S. Cl.
CPC ...... *G01S 15/8927* (2013.01); *G01N 29/0672* (2013.01); *G01N 29/262* (2013.01);
(Continued)

(58) Field of Classification Search
CPC ............. G01S 15/8927; G01S 15/8915; G01S 7/52025; G01S 7/5208; G01S 7/52096;
(Continued)

(56) References Cited

U.S. PATENT DOCUMENTS

| 4,099,251 A | 7/1978 | Minami |
| 4,271,488 A | 6/1981 | Saxe |
| 4,833,445 A | 5/1989 | Buchele |
| 5,722,412 A | 3/1998 | Pflugrath et al. |

(Continued)

FOREIGN PATENT DOCUMENTS

WO     WO 2016/077822     5/2016

OTHER PUBLICATIONS

Song, T.K., and Greenleaf, J.F., Abstract of "Ultrasonic Dynamic Focusing Using an Analog FIFO and Asynchronous Sampling", UFFC IEEE Trans., v41(3), May 1994.
(Continued)

*Primary Examiner* — Krystine E Breier
(74) *Attorney, Agent, or Firm* — Blynn L. Shideler; Krisanne Shideler; BLK Law Group

(57) ABSTRACT

An ultrasound beamformer architecture performs the task of signal beamforming using a matrix of analog random access memory cells to capture, store and process instantaneous samples of analog signals from ultrasound array elements and this architecture provides significant reduction in power consumption and the size of the diagnostic ultrasound imaging system such that the hardware build upon this ultrasound beamformer architecture can be placed in one or few application specific integrated chips (ASIC) positioned next to the ultrasound array and the whole diagnostic ultrasound imaging system could fit in the handle of the ultrasonic probe while preserving most of the functionality of a cart-based system. The ultrasound beamformer architecture manipulate analog samples in the memory in the same fashion as digital memory operates that can be described as an analog store—digital read (ASDR) beamformer. The ASDR architecture provides improved signal-to-noise ratio and is scalable.

10 Claims, 12 Drawing Sheets

Related U.S. Application Data

(60) Provisional application No. 62/079,855, filed on Nov. 14, 2014.

(51) Int. Cl.
*G10K 11/34* (2006.01)
*G01N 29/06* (2006.01)
*G01N 29/26* (2006.01)
*A61B 8/00* (2006.01)

(52) U.S. Cl.
CPC ........ *G01S 7/5208* (2013.01); *G01S 7/52025* (2013.01); *G01S 7/52096* (2013.01); *G01S 15/8915* (2013.01); *G10K 11/346* (2013.01); *A61B 8/4472* (2013.01); *G01N 2291/106* (2013.01)

(58) Field of Classification Search
CPC ........ G01N 29/0672; G01N 2291/106; G10K 11/346; A61B 8/4472
See application file for complete search history.

(56) References Cited

U.S. PATENT DOCUMENTS

| | | |
|---|---|---|
| 6,126,602 A | 10/2000 | Savord et al. |
| 6,500,120 B1 * | 12/2002 | Anthony ............... G01S 7/5208 600/437 |
| 6,705,995 B1 | 3/2004 | Poland et al. |
| 8,220,334 B2 | 7/2012 | Klessel et al. |
| 9,867,594 B2 * | 1/2018 | Hayashi ............. G01S 7/52038 |
| 2004/0015079 A1 | 1/2004 | Berger et al. |
| 2008/0262351 A1 | 10/2008 | Scampini |
| 2010/0152587 A1 * | 6/2010 | Haider .................... A61B 8/00 600/459 |
| 2011/0213251 A1 | 9/2011 | Robinson |

OTHER PUBLICATIONS

Haller, G.M.; Wooley, B.A., "A 700-MHz switched-capacitor analog waveform sampling circuit," IEEE Journal of Solid-State Circuits, v.29(4), pp. 500-508, Apr. 1994.

Kai E. Thomenius, "Recent Trends in Beamformation in Medical Ultrasound", IEEE Ultrasonics Symposium 2005.

* cited by examiner

ULTRASOUND BEAMFORMING SYSTEM AND METHOD BASED ON ANALOG RANDOM ACCESS MEMORY ARRAY

RELATED APPLICATIONS

This application is a continuation of International Patent Application Serial Number PCT/US2015/060861, which published May 19, 2016 as publication WO 2016/077,822 which publication is incorporated herein by reference. International Patent Application Serial Number PCT/US2015/060861 claims the benefit of U.S. Provisional Patent Application Ser. No. 62/079,855, filed Nov. 14, 2014 entitled "Ultrasound Beamforming System and Method Based on Analog Random Access Memory Array."

BACKGROUND INFORMATION

1. Field of the Invention

The present invention relates to ultrasonic beamforming, more specifically the present invention relates to an analog store, digital read (ASDR) ultrasound beamforming system and associated method.

2. Background of the Invention

There are number of technological areas in which analog memory devices are being used successfully such as digital storage oscilloscopes, X-ray detectors and high energy particle tracking applications. Early predecessors of this technology can be traced to digital oscilloscopes and waveform capturing devices based on Fast-In-Slow-Out (FISO) principle such as one described in U.S. Pat. Nos. 4,271,488 and 4,833,445 which are incorporated herein by reference. The '445 patent depicts the fast, high resolution FISO system, while the '488 patent describes an acquisition system that uses an analog memory matrix built of sample-hold cells arranged in rows and columns to form an M×N matrix that may be implemented on a single integrated-circuit (IC) chip.

The idea of a matrix analog memory device on an IC was further developed by Stewart Kleinfielder who produced a range of multichannel transient analog waveform digitizer chips used to capture data from detectors in neutrino physics experiments, as well as by other contributors (see Kleinfelder, S. A., "A 4096 Cell Switched Capacitor Analog Waveform Storage Integrated Circuit", IEEE Transactions on Nuclear Science, NS-37, No. 1, February 1990.; and Kleinfelder, S. A., "Advanced Transient Waveform Digitizers," SPIE Particle Astrophysics Instrumentation Proc., v. 4858, pp. 316-326, August 2002.) Additional informative background material can be found in U.S. Pat. Nos. 4,099,251; 5,722,412; 6,126,602; and 8,220,334; and U.S. Pat. App. Pub. Nos. 2004-0015079A1; 2008-0262351A1; 2010-0152587A1; 2011-0213251A1. See also Haller, G. M.; Wooley, B. A., "A 700-MHz switched-capacitor analog waveform sampling circuit," IEEE Journal of Solid-State Circuits, v. 29(4), pp. 500-508, April 1994 and Kai E. Thomenius, "Recent Trends in Beamformation in Medical Ultrasound", IEEE Ultrasonics Symposium 2005. The above identified patents and published patent applications are incorporated herein by reference.

In medical diagnostic ultrasound, there were several attempts to use analog memory for ultrasound signal beamforming, notably the scheme named Pipelined Sampled— Delay Focusing proposed by Song, T. K., and Greenleaf, J. F., in "Ultrasonic Dynamic Focusing Using an Analog FIFO and Asynchronous Sampling", UFFC IEEE Trans., v41(3), May 1994, where variably delayed analog samples in each channel were stored in an analog memory buffer build as a FIFO and summed by an analog adder before the digitization. The analog memory beamformers described in U.S. Pat. Nos. 6,500,120 and 6,705,995, both of which are incorporated herein by reference, can be seen as the variations of that pipelined sample-delay scheme.

Ultrasound imaging, such as in medical diagnostic, begins with sending specially constructed ultrasonic signals (pulses, waves or wave packets) into the subject, e.g., tissues in medical diagnostics (or turbine blades for jet engine inspection, etc.) The pressure pulse propagates in depth while attenuating and scattering on the acoustic impedance interfaces (such as a boundary between different tissues) along the way. These scattered echoes are picked up by the receiving ultrasound array and from this data the tissue composition along the pulse propagation path is reconstructed as a single scan line. Then, the next pulse is sent into a different direction and the process of receiving scattered (or attenuated as in transmission tomography) ultrasound signals back to the sensor array, and the interpretation of the results is repeated until a required 2-D slice (B-mode frame) or a 3-D volume is assembled out of separate scan lines.

In order to increase the spatial and contrast (magnitude) resolution of a signal coming from the certain spatial location within the tissue, the ultrasound array needs to be focused on that location. Thus, in the course of pressure pulse propagation in the tissue, the receiving array needs to constantly shift its focus following the pulse current position. Therefore, one of the first steps in processing the raw data is called beamforming in which signals coming to different elements of the array are time-shifted before they will be added to one another. As a rule, the beamforming applies to both, transmit and receive signals.

FIG. 1 illustrates the first method used in forming ultrasound images, also known as analog beamforming. Generally, the ultrasound imaging device consists of an ultrasonic array 106 divided to a number of independent elements 107 or channels (typically to 64 or 128 elements in linear or curved 1D array). During the transmit stage of interrogation, the transmit beamformer sends variably delayed electric pulses to the elements of the ultrasound array 106. The relative delays between the signals is constructed in such a way that ultrasonic pulses emitted by elements 107 of the array 106 would arrive to the predetermined spatial point 100 (focal point P) simultaneously, with their phases aligned to achieve a coherent summation of wavelets coming from all elements 107 of the array 106. This wave would scatter at the point 100 and part of this spherical scattered wave would travel back to the elements 107 of the array 106. Each element 107 would convert pressure variations in the incoming wave into the voltage variation output 108. The portion of this scattered wave that reaches a face surface of an array element 107 can be seen as a wavelet 102 that travels along the ray 104 that connects the scattering point 100 and the face of the element 107. Depending on the mutual position of the scattering point 100 and the specific element 107 of the array 106, the path 104 would vary from the shortest one equivalent to radius R0 105 to the longest one. The spatial difference ΔDi between the shortest path 105 and path from the point 100 to the i-element of the array 106 translates into the time delay Δti between the arrivals of signals 108. The task of the receive beamformer is to modify the time differences between the signals 108 from all elements 107 participating in beamforming and sum them in accordance with the directions of the beamforming algorithm. For example, such a beamforming algorithm may require removing the time delays Δt from all arrived signals and sum such processed signals (delay-sum algorithm), in effect focusing the array to the point P. It can be seen that workings of transmit and receive beamformers are mutually reciprocal, thus, describing the works of the receive beamformer is also a description of the solutions for the transmit beamformer.

The ways received signals are processed define the type of the beamformer. In the analog beamformer shown on FIG. 1 signals 108 were first amplified by voltage controlled amplifier (VCA) 110 to compensate the signal attenuation, then, a delay circuit 112 was used to time shift the signals to compensate the delays in arrival, then such aligned signals 114 were summed in analog summing circuit 116 and the output signal 118 was digitized by analog-digital converter (ADC) 120 producing output digital signal 122 that was stored in memory and used by the back-end processor to reconstruct B-mode or Doppler images. The advantage of such design is the simplicity of the hardware. The disadvantages include poor time discrimination and low refresh rate of the analog design elements 112 (no dynamic beamforming) as well as irreversibility of the beamforming process such that only one beamforming algorithm can be applied to the captured signals.

The second common type of the beamformer used in ultrasound imaging is commonly known as the digital beamformer (see FIG. 2). In the digital beamformer, voltage signals 108 from the elements of the array 106 are amplified by the voltage controlled amplifier (VCA) 110 to compensate the signal attenuation, then, the signal in each channel is digitized at a certain sampling rate by channel ADC 124 that outputs digitized signal to the memory or First-In-First-Out (FIFO) registers where signals are shifted in accordance with the beamforming algorithm (for example such that to remove arrival delay Δt), then such processed digital data 128 from each participating channel are summed by digital adder 130 and output data 122 are written to the memory for further processing. Alternatively, elements 126 and 130 can be realized as software blocks of beamforming algorithm. The advantages of digital beamformer, such as shown in FIG. 2 are its speed and precision which allows implementation of the dynamic beamforming and the possible realization of multiple beamforming strategies on the same data volume. The disadvantage is hardware complexity; manifesting in larger hardware size, higher cost, and higher power consumption (heat generation).

For clarity, the analog and digital beamformers schematics shown on FIGS. 1 and 2 were simplified by removing the multiplexing stage. In reality, as known to those in the art, having the number of processing channels equal to the number of the arrays' elements is a very expensive proposition. Thus, the array can have 64, 128, 256 or greater number of elements but the beamformer would have typically 32 or 64 channels and an analog multiplexing circuitry that would select elements of the array 106 into the current aperture. Also for the same reasons, cable and signal connectors that connect elements of array 106 to the analog front-end electronics are not shown, even though they do affect the system cost and signal quality.

From the description of the beamforming process it can be seen that the signal coming from the output of the array element 107 is processed independently from the signals coming from the other elements up to the output of the beamformer where all of the signals are combined. Thus, this text will refer to this signal path from the element 107 to the input of adder 116, 130 (or 136) as a "signal path" or "beamforming channel" or simply as "channel" 109. There remains a need in the art to reduce the size and power requirements of diagnostic ultrasound imaging and to utilize beamforming architecture to accomplish this goal.

SUMMARY OF THE INVENTION

An Analog Store Digital Read (ASDR) ultrasound beamforming architecture is presented which performs the signal beamforming task using a matrix of sample/hold cells to capture, store and process instantaneous samples of analog signals from ultrasound array elements. This architecture provides significant reduction in power consumption and size of the diagnostic ultrasound imaging system such that the hardware build upon ASDR ultrasound beamformer architecture can be placed in one or few application specific integrated chips (ASIC) positioned next to the ultrasound array. The whole diagnostic ultrasound imaging system could fit in the handle of the ultrasonic probe while preserving most of the functionality of a cart-based system. The ASDR architecture provides improved signal-to-noise ratio and is scalable.

One aspect of the present invention provides an Analog Store Digital Read ultrasound beamforming method implementing sequential write and arbitrary read operations in Analog Random Access Memory (ARAM) for an ultrasound imaging system comprising the steps of: i) Providing an ultrasonic array formed of individual ultrasonic array elements configured for transmission and receiving; ii) Dividing the individual array elements into individual channels, wherein each channel comprises at least one array element; iii) Creating a receiving input signal for each channel from inputs received from each array element of the channel; iv) Sampling each receiving input signal for each channel at a sampling rate and storing the sampled data in a bank of sample-hold cells which are associated with that channel, wherein the bank of sample-hold cells form an analog random access memory for the sampled receiving input signal; v) Selecting at least one sample-hold cell data from at least one channel for each particular output time for each beamforming instance in accordance with a beamforming algorithm; vi) Summing all of the selected sample-hold cell data from the associated channels for the beamforming instance forming an analog beamformed received signal sample for the beamforming instance; and vii) Digitizing the analog beamformed received signal sample.

One aspect of the present invention provides an Analog Store Digital Read ultrasound beamforming method implementing arbitrary write and sequential read operations in ARAM for an ultrasound imaging system comprising the steps of: i) Providing an ultrasonic array formed of individual ultrasonic array elements configured for transmission and receiving; ii) Dividing the individual array elements into individual channels, wherein each channel comprises at least one array element; iii) Creating a receiving input signal for each channel from inputs received from each array element of the channel; iv) Sampling each receiving input signal for each channel at a sampling rate and storing the sampled data in a bank of memory cells, wherein the bank of memory cells form an analog random access memory, wherein the present sample from each channel participating in this beamforming instance is added to the memory cell with address defined by the beamforming algorithm for this particular time instance, wherein each memory cell is associated with a sample clock time instance, and wherein each memory cell participating in the beamforming instance sums the selected samples from plurality of channels selected by the beamforming algorithm forming an analog beamformed received signal sample for the beamforming instance; and vii) Digitizing the analog beamformed received signal sample.

One aspect of the present invention provides an Analog Store Digital Read ultrasound beamforming method implementing arbitrary write and arbitrary read operations in ARAM for an ultrasound imaging system comprising the steps of: i) Providing an ultrasonic array formed of individual ultrasonic array elements configured for transmission and receiving; ii) Dividing the individual array elements into individual channels, wherein each channel comprises at least one array element; iii) Creating a receiving input signal for each channel from inputs received from each array element of the channel; iv) Sampling each receiving input signal for each channel at a sampling rate and storing the sampled data in a bank of memory cells, wherein the bank of memory cells form an analog random access memory, wherein analog random access memory has at least one row per channel and the number of columns being equal or larger the number produced by multiplying the sampling rate to maximum delay needed to correct, wherein the instantaneous sample from each channel participating in this beamforming instance is added to at least one memory cell with addresses thereof defined by the beamforming algorithm for this particular time instance, wherein each memory cell in the row is associated with a sample clock time instance each memory cell in the column in associated with the scan line, and wherein each memory cell participating in the beamforming instance sums the selected samples from plurality of channels selected by the beamforming algorithm forming an analog beamformed received signal sample for the beamforming instance; and vii) Digitizing the analog beamformed received signal sample.

One aspect of the present invention provides an Analog Store Digital Read ultrasound beamforming system for an ultrasound imaging system comprising an ultrasonic array formed of individual ultrasonic array elements configured for transmission and receiving, wherein the individual array elements are formed into individual channels, wherein each channel comprises at least one array element and each channel uses less than 40 milliwatts in operation.

One aspect of the present invention provides an Analog Store Digital Read ultrasound beamformer for an ultrasound imaging system comprising: i) An ultrasonic array formed of individual ultrasonic array elements configured for transmission and receiving, wherein the individual array elements are grouped into individual channels, wherein each channel comprises at least one array element; ii) A receiving input signal control circuitry for creating receiving input signals for each channel from inputs received from each array element of the channel; iii) A plurality of banks of sample-hold cells with each bank of sample-hold cells associated with one channel, wherein the beamformer is configured for sampling each receiving input signal for each channel at a sampling rate and storing the sampled data in one bank of sample-hold cells which are associated with that channel, wherein the bank of sample-hold cells form an analog random access memory for the associated sampled receiving input signal; iv) A beamforming processor configured for selecting at least one sample-hold cell data from at least one channel for each beamforming instance in accordance with a beamforming algorithm; v) An analog summation element for summing all of the selected sample-hold cell data from each channel for each beamforming instance and forming an analog beamformed received signal sample for the beamforming instance; and vi) An Analog-to-Digital converter for digitizing the analog beamformed received signal.

These and other advantages of the present invention will be clarified in the brief description of the preferred embodiment taken together with the drawings in which like reference numerals represent like elements throughout.

DESCRIPTION OF THE PREFERRED EMBODIMENTS

Figure 1:
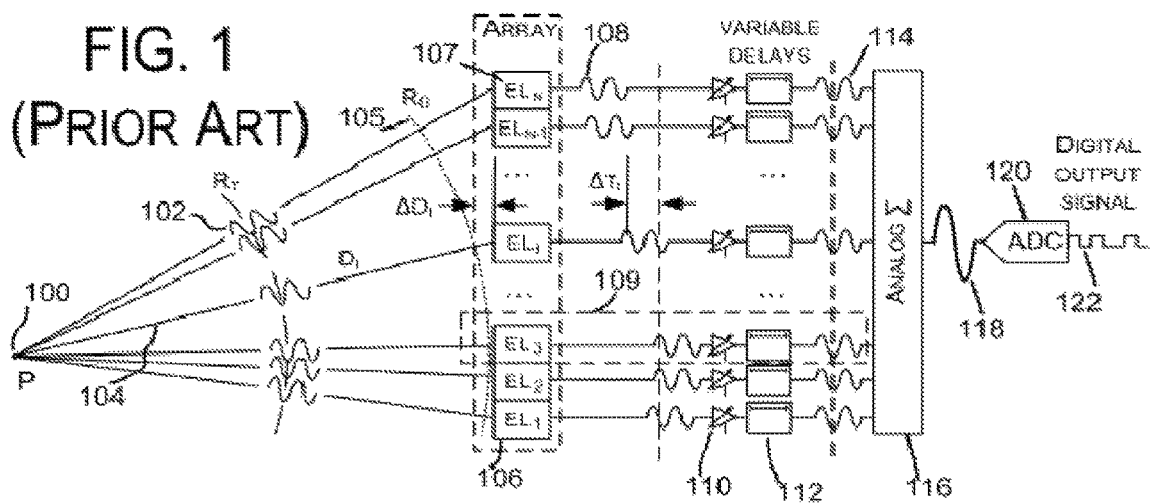
FIG. 1 is a schematic representation of a prior art analog beamformer.
Figure 2:
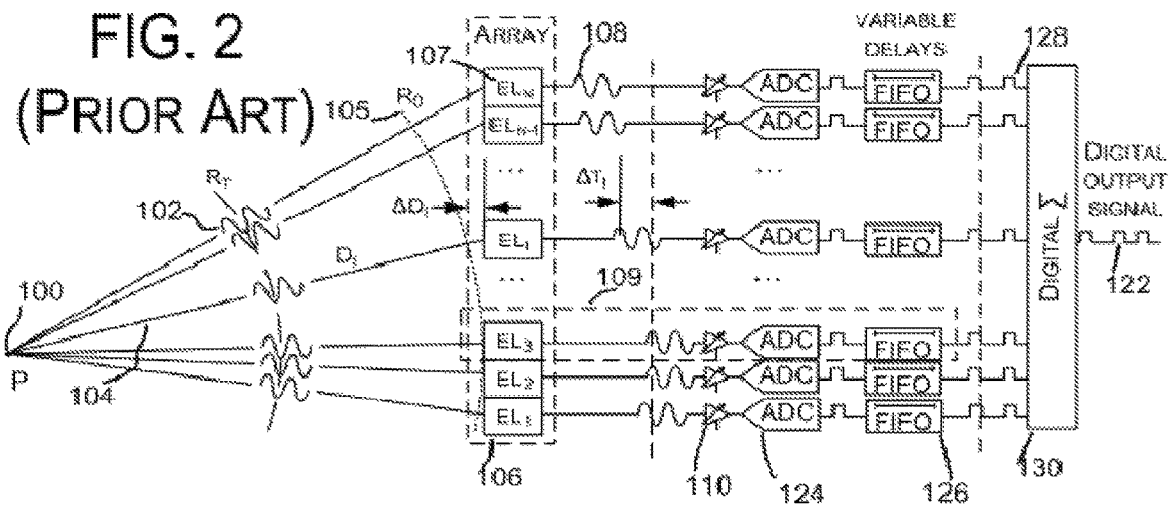
FIG. 2 is a schematic representation of a prior art digital beamformer.

The present invention relates to ultrasound diagnostic systems, such as used in medical diagnostic systems for medical human and animal applications. Some aspects of the present invention are understood in connection with WO/2014/125371, corresponding to PCT/IB2014/000281 which is incorporated herein by reference. The present invention is also applicable to non-destructive testing/evaluation (e.g., pipeline testing, airframe testing, turbine blades testing, bridge and structural testing, manufacturing testing (e.g. metal working rolls)). Ultrasonic testing is a type of nondestructive testing commonly used to find flaws in materials and to measure the thickness of objects. Frequencies of 1 to 50 MHz are common, but for special purposes other frequencies are used. Inspection may be manual or automated and is an essential part of modern manufacturing processes. Most metals can be inspected as well as plastics and aerospace composites. Lower frequency ultrasound (50-500 kHz) can also be used to inspect less dense materials such as wood, concrete and cement. The present invention is also applicable to geophysical exploration and sonar applications, and generally any ultrasound imaging (or image-like) applications requiring beamforming for transmission and/or receiving. The present invention is directed in particular to the way signals coming from the elements of an ultrasonic array (receive beamformer) and going to the elements of the same array (transmit beamformer) are treated. The invention describes a beamformer system that provides better image quality combined with significant reduction in systems' size, power consumption and production cost as compared to current systems. Thus, even though a main application of this invention is in medical ultrasound, this beamforming architecture, and the hardware and software built upon its principles, can be used in other areas such as non-destructive testing, sonar, radar, terahertz, infrared, optical imaging systems or for seismic geophysical exploration.

The general idea of the new design is to create a mixed beamformer that would use digital control and manipulation of analog signals from the transducer array elements. Such design allows radical minimization of the hardware volume and power consumption of electronic circuitry, opening a possibility for the development of ultraportable ultrasound machines and advances in premium systems. There are several basic approaches to the manipulation of the analog signals to build an ASDR beamformer, including: a) Sequential Write—Sequential Read (SWSR) to and from analog memory. This principle was first used in event capturing devices when some fast signal is recorded to ARAM at high speed and later replayed and digitized at slower sampling speed for nuclear physics detectors, (Kleinfelder, S. A., "A 4096 Cell Switched Capacitor Analog Waveform Storage Integrated Circuit", IEEE Trans. Nucl. Sc. NS-37(1) 1990). As an ultrasound beamformer this architecture is realized in Pipelined Sampled—Delay Focusing beamformer (Song, T. K., and Greenleaf, J. F., "Ultrasonic Dynamic Focusing Using an Analog FIFO and Asynchronous Sampling", UFFC IEEE Trans., v41(3), 1994), where non-uniform sampling clocks were used to variably delay analog samples in each channel before they are captured and stored in an channels' analog FIFO buffer and samples from all channel FIFO's sequentially read and summed by an analog adder before the digitization. A variation of this scheme in which samples are written sequentially and then read with a proper delay injected via "slipping" of one of few sampling periods are described in U.S. Pat. Nos. 6,500,120 and 6,705,995 (incorporated herein by reference); b) Sequentially Write—Arbitrary Read (SWAR) to and from the analog memory cells; b) Arbitrary Write—Sequentially Read (AWSR) to and from the analog memory cells, and c) Arbitrary Write—Arbitrary Read (AWAR) to and from the analog memory cells. These latter three approaches are subject of this invention wherein the SWAR beamformer will be described fully, and for AWSR and AWAR architectures the application describe the significant differences to ASWR design. The term "arbitrary" is used throughout the present application and it should be understood to mean "random access" as generally known in the art. Arbitrary access to memory cells is used by the beamforming algorithm to conduct the beamforming.

Figure 3:
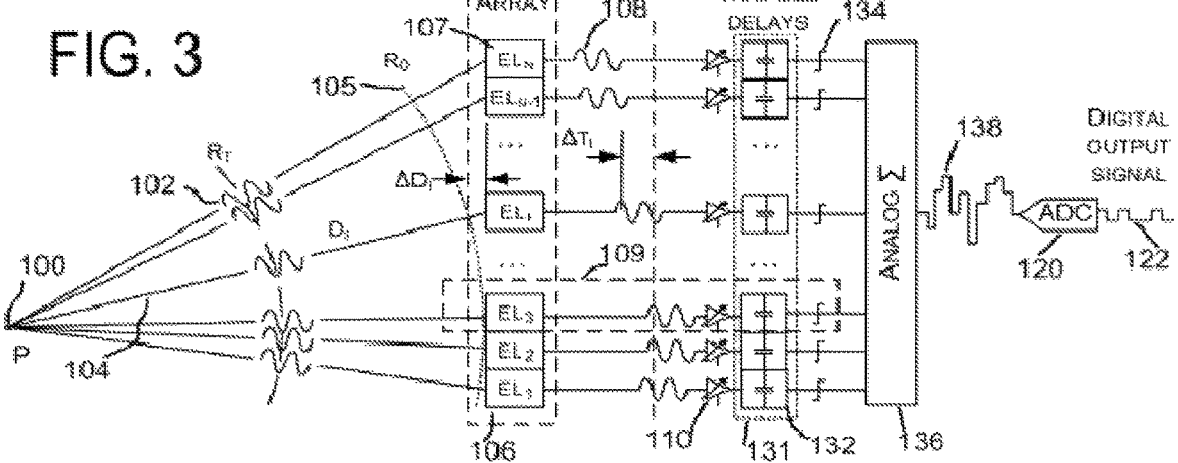
FIG. 3 is a schematic representation of an Analog Store Digital Read (ASDR) ultrasonic beamformer in accordance with one embodiment of the present invention.
Figure 4A:
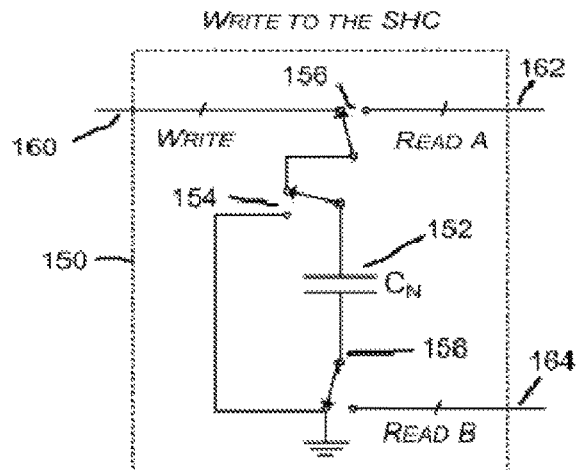
FIGS. 4A-D are schematic representation of representative Sample/Hold Cells (SHC) for use in the ASDR ultrasonic beamformer of the present invention.
Figure 4B:
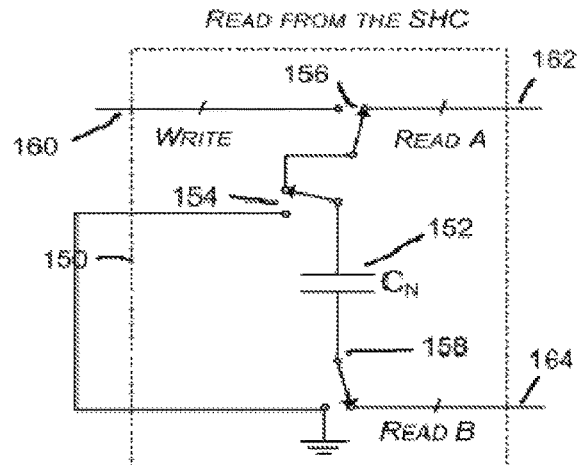
Figure 4C:
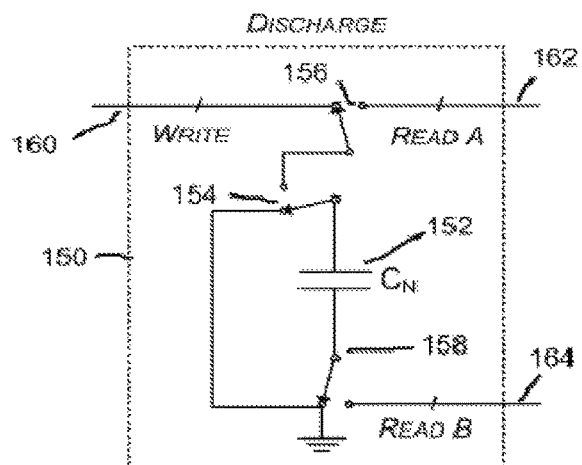
Figure 4D:
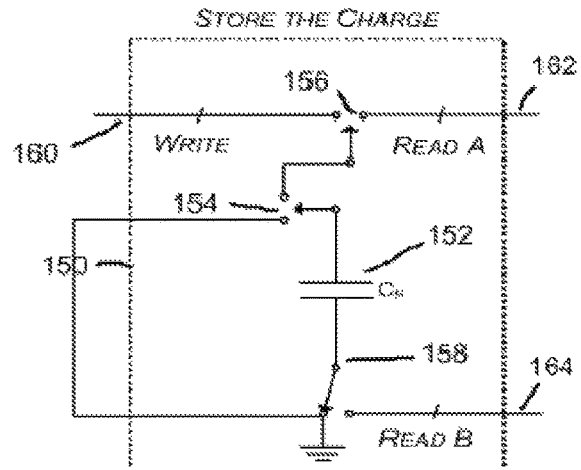

SEQUENTIAL WRITE—ARBITRARY READ BEAMFORMER ARCHITECTURE—FIG. 3 depicts a schematic outline of a beamformer build with the SWAR principle. In the beamformer of the present invention, an analog signal 108 from the element 107 of the array 106 goes through a voltage controlled amplifier (VCA) 110 to compensate the signal attenuation in the media, then is written into an array 131 of Sample-Hold Cells and at a certain sampling rate as a sequence of voltage levels. The sampling rate may be fixed or variable and also may be independent and different from the sampling rate of the reading from the sample hold cells of array 131.

Figure 10:
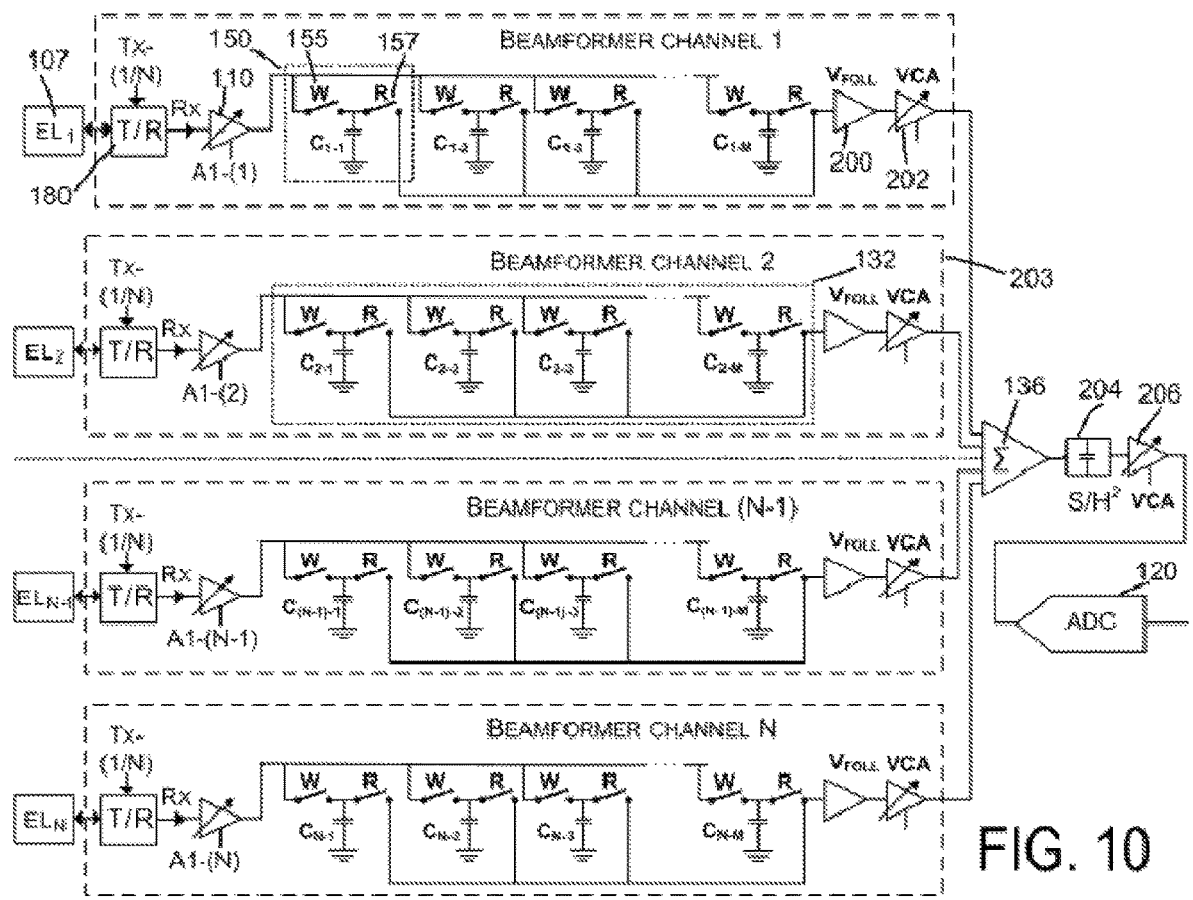
FIG. 10 is a schematic representation of a receive beamformer used in the ASDR ultrasonic beamformer of the present invention.

Each SHC array 131, also known as Analog Random Access Memory (ARAM) array 131, consists of a plurality Sample/Hold Cells 150 arranged in distinct rows or banks 132 and that have common signal lines and control switches that function in a fashion similar to conventional digital random access memory as discussed below (also refer to FIG. 10). Next, in each signal channel 109, one Sample/Hold cell 150 of one row 132 is selected in accordance with the beamforming algorithm and the samples of analog signal 134 from all channels participating in the beamforming process at this particular time moment, also known as beamforming instance, which being defined as one sampling step in execution of the beamforming algorithm, are summed by an analog summing circuit 136. The output analog signal 138 which represents the results of the beamforming as a sequence of analog samples is digitized by the analog-digital converter 120 and output data 122 is written to the memory for further processing.

In other words, the beamforming process consists of storing analog samples of continuous signals from array elements, then reading the content of certain analog memory cells in the same way that digital memory cells are read in the digital beamformer process. However, instead of adding digital representations of signals to produce the output beamformed signal, the analog representations of the same signal are summed up first and the result is digitized. Thus, the process of operating samples of analog signals in a digital manner comprises the essence of the Analog Store—Digital Read (ASDR) ultrasound beamformer system and method of the present invention. In order to describe the functions and operations of the Analog Store—Digital Read (ASDR) ultrasound beamformer the description will begin with the basic building blocks of such the device and progress up to the system level.

SAMPLE-HOLD CELL—The basic building block of the analog memory array is a Sample-Hold Cell (SHC). The design of SHC is well known and here a SHC design is used based on the storage capacitor as an example of the design; however, any device that can store an analog quantity can be used for building such a cell.

The schematic organization of a single sample-hold cell (SHC) 150 is shown on FIGS. 4A-D and 5. Main elements of the SHC are the storage capacitor 152, analog switches 154-158 that connect capacitor 152 to input analog signal line WRITE 160 and output signal lines READ A 162 and READ B 164, or to the ground. Switches 154-158 can be made based on transistors, MEMs, or other technology enabling analog switching and multiplexing.

Figure 5:
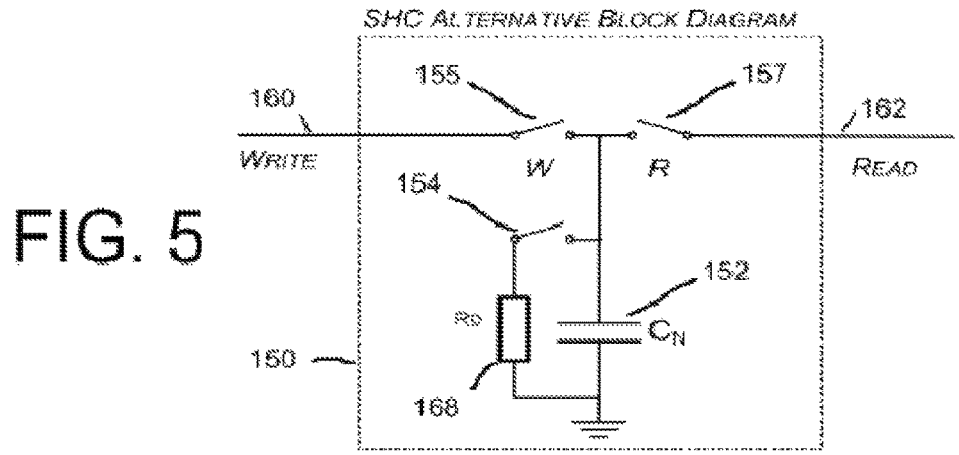
FIG. 5 is a schematic representation of an alternative SHC for use in the ASDR ultrasonic beamformer of the present invention.

FIG. 5 illustrates schematic representation of variations in the basic SHC 150 design, such as the use of "single-pole, single-throw" (SPST) Write Switch 155, another SPST Read Switch 157, an addition of bleed resistor 168 to control the capacitor discharging process through the switch 154, and joining the bottom plate of the storage capacitor 152 permanently to the signal ground. These, or any other known variation of the SHC design, are included herein.

Figure 6:
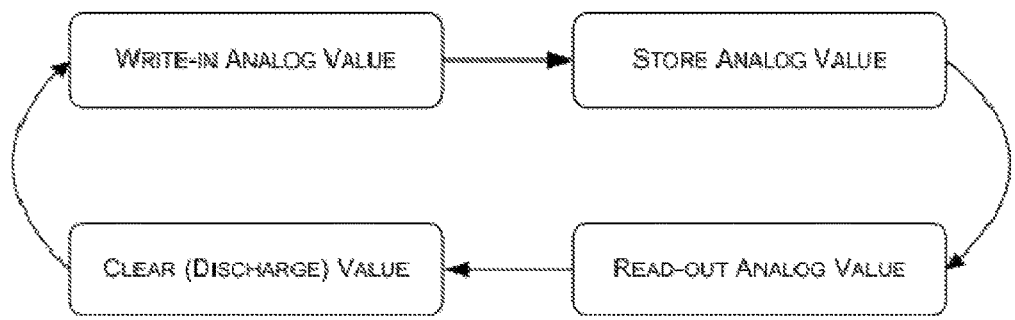
FIG. 6 is a schematic timing diagram illustrating work of the Sample/Hold Cells used in the ASDR ultrasonic beamformer of the present invention.

The SHC 150 working cycle, shown schematically in FIG. 6, consists of the following operation: writing the voltage level into the storage capacitor 152, storing the charge, reading the content of the capacitor 152, and erasing the content of the storage capacitor 152 in preparations for the next work cycle. Referring to time diagram of FIG. 7, during the write operation at time Ti, the top plate of the capacitor 152 is connected to the input analog signal line WRITE 160 via switches 154 and 156. Switch 158 connects the bottom plate of the 152 to the ground. The voltage value of V(Ti) from the output of VCA1 (110) is stored in the capacitor 152. During the time period T3 (storage operation), one or both switches 154 and 156 are in a high impedance state (open or disconnected from signal lines). After time T3 that occurs within the time period T1, the content of capacitor 152 is read. In the read operation, switch 158 connects the bottom plate of the capacitor 152 to the READ B output signal line 164 and the top plate of the capacitor 152 through switches 154 and 156 is connected to the READ A signal line 162. The discharge operation that occurs during time period T2 consists of connecting the top and bottom plates of the capacitor 152 via switches 154 and 158 to the ground directly or through the bleed resistor 168. The total time of read-store-discharge cycle (referring to FIG. 7) $\Delta t = t_{i+1} - t_i = T1 + T2$ is defined by the length of the rows (number of S/H cells) of SHC bank 109, sampling rate, and the maximum signal delays need to be corrected. The open and close state of switches 154-158 is controlled by the beamformer control circuitry that will be discussed below.

SAMPLE-HOLD CELL ARRAY—The separate sample-hold cells 150 are organized row-wise and column-wise into the Sample-Hold Cells Array 131 (or an analog random access memory or ARAM). In the preferred embodiment the number of rows 132 of the array 131 (or a number of beamformer channels 109) is typically equal to the number of elements 107 in the transducer array 106 (for example 128 elements). In other embodiments, the number of beamforming channels 109 can be smaller or larger that number. The number of columns (number of S/H cells in SHC bank 132) is defined by the sampling rate and the maximum delay in signal arrival to the elements of the transducer array 106 as explained later. For example, for a common curved medical ultrasound transducer array, like that known as C5-2/60, with a fully opened active aperture of 128 elements (total length of 60 mm) and the signal penetrated into the tissue to z=100 mm depth, the maximum signal path difference (a pulse coming from the depth z to the center of the aperture and to the aperture edge) will be around $\Delta d \approx 4.4$ mm (see FIG. 3). At a sound speed of 1540 m/s, it gives maximum delay $\Delta t \approx 2.86 \times 10-6$s. At the sampling rate of S=40 MS/s (mega samples per second) it will be necessary to capture a minimum 114 sample points to be able to compensate for the 2.86 micro-seconds delay in arrival of signals to all elements 107 of the aperture. Thus, in this case, the SHC array 131 will consist of at least 114 columns of sample-hold cells 150 in each of 128 rows 132. In other embodiments the number of columns N can be bigger than the minimum required number, but the criteria $N > \Delta t \times S$ (Samples/sec) gives the minimum estimate for the number of sample capacitors or cells 150 in each row 132.

Figure 8A:
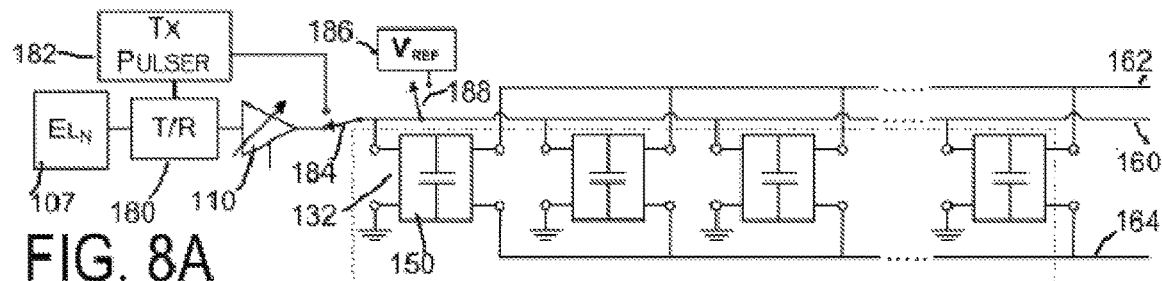
FIGS. 8A and 8B are alternative schematic block diagrams of transmit and receive beamformer channel in accordance with two embodiments of the present invention.
Figure 8B:
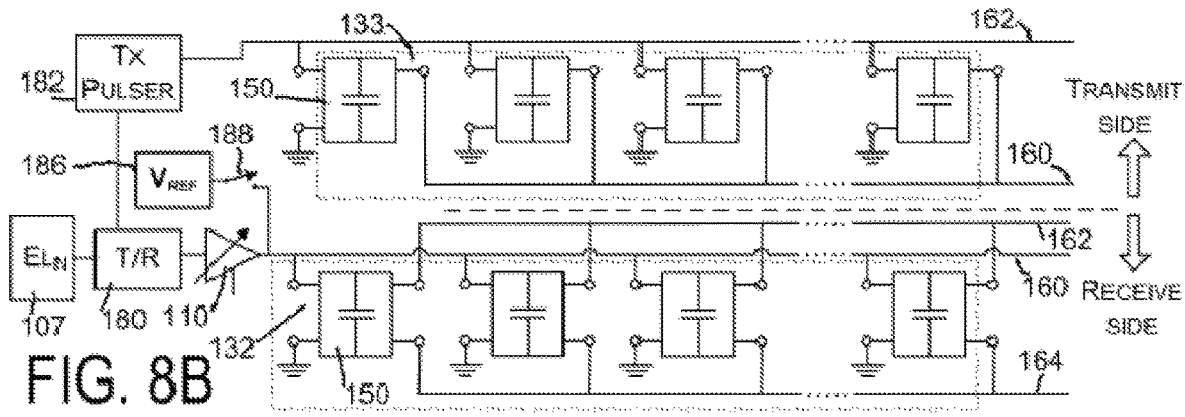

Column-wise organization of the SHC array is used for writing data into the S/H cells 150 and row-wise organization is used to read data out of the cells. In FIGS. 8A and B, two main architectures employing such an array in an ultrasound beamformer are shown. FIG. 8A displays a partial schematic diagram of one channel 109 of an ultrasound system in which a SHC row 132 is shared between the transmit and receive beamformer channel via switch 184. FIG. 8B shows a partial schematic diagram of one ultrasound channel 109 where transmit and receive beamformers have their own SHC row banks 132 and 133 to store and read analog samples. Even though banks 132 and 133 may have the same design (as shown on FIGS. 4A-D and 5), the SHC bank 133 is marked separate from the 132 to denote that they belong to two physically different arrays that may have different size values of storage capacitors 150. All S/H cells 150 belonging to the row bank 132 are connected to common signal lines 160, 162, and 164. The logic circuits controlling cells switches 152-158 allow selection of a single cell, a group, or all cells to perform read, write, store, or discharge operations in a similar fashion to the logic controlling the digital dynamic RAM operations.

TRANSMIT BEAMFORMER OPERATIONS—Referring to the FIG. 8B, the transmit phase of beamformer operations begins with writing a pulse shape into the beamformer channel transmit analog sample storage 133 in which the Digital Analog Converter or DAC (not shown) uses WRITE line 160 to write voltage level samples into cells 150 of SHC row 133. The preferred embodiment is to have a number of transmit beamformer channels 133 be equal to the number of receive channels 132 and the number of the transducer array elements 107. In other embodiments, a number of transmit channels can be bigger than the number of array elements for storing different signal shapes or smaller than the number of elements 107 down to a single channel 133 serving all elements of the array. The pulse shape is formed by a sequence of voltage samples stored in 133. In order to form the pulse, sample-hold cells 150 of SHC row 133 are sequentially connected to the input of high voltage pulser 182 connected to the transducer element 107 via transmit-receive switch 180. The pulse central frequency and the frequency content are defined by the pulse shape together with the sampling (or clock) speed at which voltage samples arrive to the input of the pulser 182. The beamforming delay for the each transmit channel is formed by the channels' own timer delaying the start of pulse forming by an appropriate number of clock cycles using for example a countdown counter or buffer.

In one embodiment, the voltage resolution of the sample-hold cells in the SHC row of transmit channel 133 can be lower than the SHC resolution in the SHC row of receive channel 132. In other embodiments, transmit channel cell resolution can be as low as 2 bits or be as high as the receive SHC resolution. The depth of the transmit SHC row 133 can vary from two cells to the number equal of the number of cells in the receive row 132.

The SHC row 133 may store not one but a number of pulse shapes sequentially, that can be rapidly selected by the transmit controller to form different pulses during the current scan line operation (for instance to form multiple focus points in one scan line generation with various central frequency pulses) or for a different scan lines generations (for example as in pulse inversion imaging).

In one embodiment, each SHC row 133 may store a pulse shape that is common for all beamforming channels or store a pulse shape that is individual for each beamforming channel or groups of beamforming channels.

The pulse shapes can be refreshed or re-written during the receive phase of beamforming, if required. The clock or sampling frequency of the transmit beamformer circuitry can be the same as clock speed of the receive beamformer or higher or lower as these speeds are independent. Further the sampling frequency may be variable. In one embodiment, the sampling speed of the transmit beamformer can be changed programmatically while in transmit to change the frequency content of the transmit pulse while preserving its' recorded shape.

The other possible embodiment of transmit-receive channel architecture is shown in FIG. 8A. In this embodiment, transmit and receive parts of beamforming channel share the same SHC array 132 via switch 184. The transmit and receive operation proceeds in the same fashion as described above with the exception that at the end of receive cycle the WRITE line 160 is disconnected from the output of 110 and a pulse shape data from the external DAC is written sequentially into SHC cells of array 132 while the last receive beamforming events occur in the far end of the SHC array.

RECEIVE BEAMFORMER OPERATIONS—Referring to the schematic of the beamforming channel 109 of FIG. 8B, the piezo-element 107 (part of the transducer array 106) converts electric energy into mechanical vibrations during the transmit stage and mechanical vibration energy into electric signals during the receive stage. The transmit-receive switch 180 connects the element 107 to the output of high voltage transmit pulser 182 or to the input of the amplifier 110 (that may internally consist of a low-pass filter, a low noise amplifier (LNA) stage and a VCA as a second stage for time-gain compensation). The filtered, amplified signal from the output of the VCA 110 is connected to the WRITE signal lane 160 that connects all sample-hold cells 150 that form the SHC row 132. Instead of the output of VCA 110, the signal line 160 can be connected via switch 188 to the reference voltage source 186 which allows testing the performance and calibration of cells in the bank 132 by writing and reading the calibrated voltage levels. Output READ signal lines 162 and 164 allow connecting any storage capacitor of any cell 150 to the input of the current or voltage follower or a summing circuit or allow to directly connect selection of storage capacitors 150 sequentially when no apodisation is required (for example, in sub-aperture beamforming).

Figure 7:
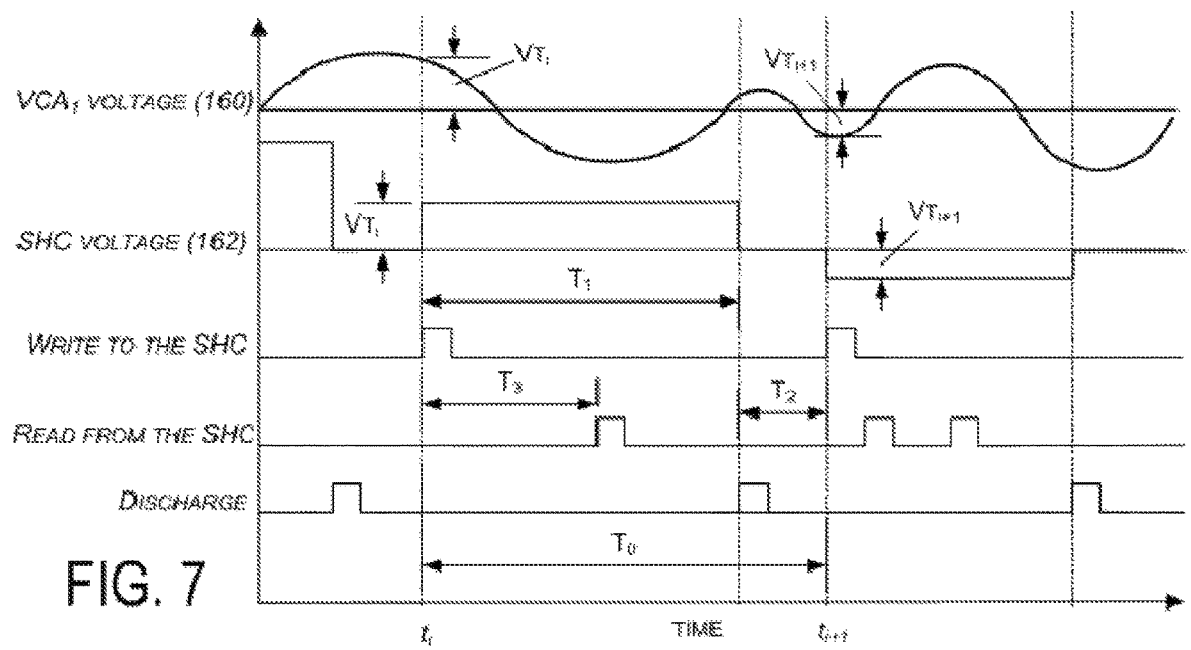
FIG. 7 is a timing diagram illustrating work of the ASDR ultrasonic beamformer of the present invention.

During the receive stage, voltage levels from VCA 110 are sampled with a certain frequency (sampling rate) and stored in consecutive cells 150 until the last cell has received a sample to store. At that point, the write operation starts again with the first cell (proceeding by the cell discharge operation as shown in FIGS. 6 and 7). In some embodiments the discharge operation may not be included and the old cell's content is replaced by the new one during the write operation. The writing operation begins at the moment when the signal scattered from the minimum depth set by the user reaches the array and continues until the signal from the pre-set maximum depth comes to the farthest element of the array participating in beamforming. Instead of writing and storing the whole time-pressure history for all elements of array in the course of receiving scattered data for the creation of a scan line, the present invention uses a sliding window approach, storing only the current part that is used in the creation of current samples of the beamformed signal.

Figure 9:
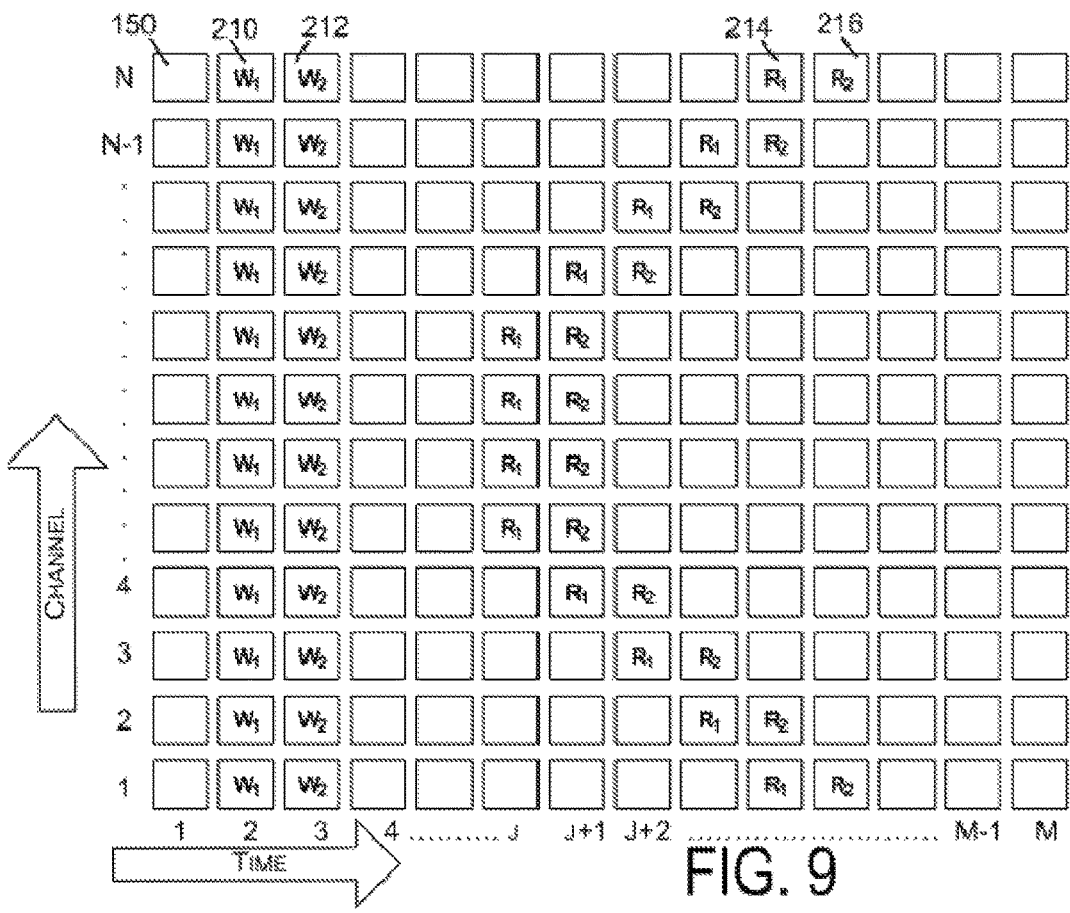
FIG. 9 schematically illustrates the process of writing to and reading from the SHC array used in the ASDR ultrasonic beamformer of the present invention.

After the start of data acquisition and filling enough columns, the reading (beamforming) operation begins. FIG. 9 illustrates how the writing to and reading from the SHC array occurs. In it, each square represents one sample-hold cell 150 with N rows (beamforming channels) and M columns. At time instance tJ+1 samples of voltage levels from corresponding VCAs 110 are written into column 210 marked by the symbol W1. At the same time, cells 214 marked by R1 are selected by the beamforming algorithm for a creation of the current output beamformed sample. The content of these cells is read and summed by a summing circuit. At the next sampling interval time tJ+2 S/H cells 212 marked by W2 are written and cells 216 (R2) are read. When the read operation reaches the end of the SHC array it folds over to the first column, in the same way as the analog sample write operation does. Since the present system has separate signal lines for read and write, these operations could be done simultaneously. It is desirable to keep the number of columns in the array a bit bigger than the minimum number required, so the read and write operation would not overlap. In some embodiments the system divides the whole array 131 column-wise into a few independent blocks allowing a write operation in one column-wise memory block, discharge in the next one, while the rest of blocks is reserved for the read operation. For instance, the system divides column-wise the array 131 consisting of 128×128 elements into eight blocks of 128×16 SHC cells each. Then, at some moment of time block 5 is used for writing data from 128 channels, block 6 for discharging it's content, and blocks 7, 8, and 1-4 are used for reading and beamforming. Accordingly a segmented single signal line may be used for accessing the cells instead of separate read and write lines. The freedom in selecting which cells would participate in the beamforming instance allows reusing the stored sampling data to implement not just a single beamforming algorithm, but obtain a number of various beamforming scenarios on the same block of data, similarly as it can be performed with stored channel data in digital beamforming architecture.

Generally speaking, write operations do not need to be performed on consecutive columns of S/H cells. The cell's addresses can be random as long as the memory controller keeps the score. Writing data column-wise is a convenient option, however SHC arrays can be also built to be used as random access analog memory ARAM with voltage level samples from an element being stored in random locations (no hard channel and timing links). Potential advantages of the approach are enabling freedom to choose the depth of SHC row banks (channels) and size of aperture (number of rows or transducer elements). Among potential disadvantages is that analog multiplexors are needed to switch channels and the writing speed may be lower, however, such a design option may be considered for some applications.

Also, sampling rates for Sample-Hold Cells array 132, adder 136 and ADC 120 does not need to be the same and/or be synchronized. In some embodiments it may be desired to have a single clock to control all three blocks, in other embodiments it may be desired to have a phase difference between read, write and digitize operation. In yet another embodiment it may be desired to have different frequencies phase-linked or completely independent, to control the operation of Sample-Hold Cells array 132, adder 136 and ADC 120. There may be benefits to have all three functional blocks functioning at independent sampling rates with different frequencies and phases and to have the capability to dynamically adjust sampling clock for every functional block independently as addressed in more details below.

RECEIVE BEAMFORMING SUMMING OPERATIONS—The beamforming summation can be done with voltage or with current values of analog samples stored in SHC 150. Referring to FIGS. 9 and 10, in the beamforming instance at time tJ+1 after cell 150 (marked by R1) in each beamforming channel 132 was selected by the beamforming algorithm, the storage capacitor 152 is connected to the input of voltage or current follower 200 by signal lines READ A (162) and READ B (164). In one embodiment, the voltage follower 200 is connected to voltage controlled amplifier 202 that is used for forming of aperture apodisation and for capacitor calibration compensation. The current active aperture span is controlled by setting apodisation value to zero for the channels that will not be participating in current beamforming instance. In another embodiment, voltage follower 200 and VCA 202 can be combined in one circuit. In yet another embodiment, 200 is a current follower. In another embodiment one plate of storage capacitor 152 is permanently attached to the signal ground and signal line READ B 164 is absent.

In one embodiment each receive beamforming channel has its own 200 and 202 amplifiers. Another embodiment may have a reduced number of 200 and 202 amplifiers with analog multiplexors to connect the selected beamforming channels with the aperture formed by the multitude of 200 and 202 amplifiers. Yet another embodiment may have VCA 202 be removed or be replaced by an analog switch for active aperture selection.

For convenience, the system defines the analog channel AC 203 that includes all of the elements and functional blocks that participate in the analog signal acquisition, storing and processing from the output of array element 107 to the voltage sample on the output VCA 202. Output of VCA 202 (or AC 203) represent a properly delayed, apodised and compensated analog channel sample.

In the voltage summing scheme, the summing circuit 136 receives instances of voltage samples from all beamforming channels, sums them and outputs the result. If the current summing approach is used, the circuit 136 is the current summing circuit. In another embodiment summing is achieved not with the content of actual storage capacitors 152 but their content first copied into temporary storage capacitors that are used for summing. In yet another embodiment, summing is achieved by connecting all storage capacitors 152, or temporary storage capacitors, participating in the beamforming event serially in which line 164 of the first capacitor is connected to line 162 of second row capacitor etc. until the last capacitor is connected. The sum value is then read from line 162 of the first capacitor and line 164 of the last capacitor.

The output of the summing circuit 136 is connected to a secondary Sample-Hold Cell 204, VCA 206, and Analog-Digital Converter 120. The output of analog digital converter 120 is a digitized beamformed RF signal. Further, elements 204 and 206 may be absent from the schematic, be attached in reverse order, or be internal elements of ADC 120. The VCA 206 may include a low pass filter.

In one embodiment, in-phase/quadrature (I/Q) data is generated by directly sampling the received radio frequency (RF) signal from the output of ADC 120. In another embodiment the output of VCA 206 also may be connected to a conventional I/Q demodulation sampling circuit.

Figure 11:
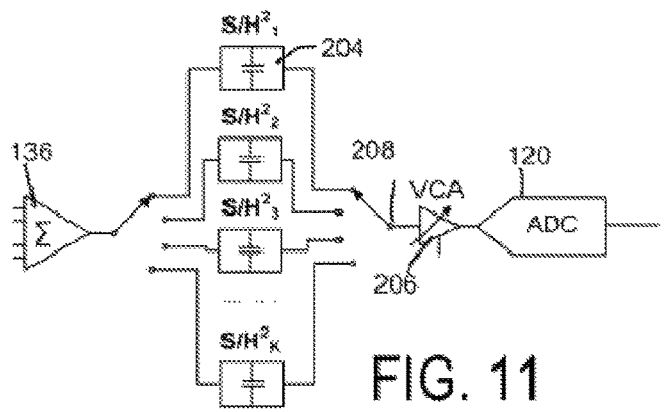
FIG. 11 is a schematic block diagram of a second stage Sample/Hold Cell array in accordance with one aspect of the present invention.

SECONDARY SHC—The secondary Sample-Hold Cell 204 has the same design as S/H cell 150. In one embodiment a single SHC 204 is used to store the current results of summing in element 136. In another embodiment, as shown on FIG. 11, a number of S/H cells can be used for temporarily storing results of summing the different beamforming algorithms working on the same channel's data block before their analog to digital conversion via switch 208 and secondary VCA 206 (VCA may be absent or replaced by a voltage follower). In yet another embodiment, the secondary SHC array may have a similar size and a similar use to the primary SHC array 131. In it, primary array 131 is used for sub-aperture beamforming, operating on the group of closely spaced transducer elements and the secondary SHC array is used for beamforming the results of pre-beamforming as described below. In yet another embodiment there may be a tertiary SHC array working on results of sub-aperture beamforming of the secondary SHC array and so on.

VARIABLE SAMPLING CLOCK OPERATION—It is well known in art that the beamforming process requires proper alignment of phases of all channels participating in a beamforming event in order to minimize the focusing delay error (or delay quantization error) that degrades the signal-to-noise ratio of the output beamformed signal and resulting image dynamic range. This requirement sets the sampling clock rate well above the Nyquist frequency. Earlier works, (G. F. Manes, et. al., "Design of a Simplified Delay System for Ultrasound Phased Array Imaging," IEEE Trans. Son. Ulrrason., vol. SU-30, 1984) set the minimum criteria as eight times the central frequency of the transducer. Modern, more advanced systems with the wideband transducers require delay resolutions in the order of $\frac{1}{16}$ the signal period (C. Fritsch, et. al., "Beamforming with a reduced sampling rate", Ultrasonics. v40(1-8), 2002). At the set sampling rate, the delay quantization error increases from low end of the signal bandwidth to its high end, such that the high frequencies in the signal, which already suffers from the frequency dependent attenuation, are affected the most. Therefore, it is reasonable to set the clock rate as function of the highest frequency in the transducer bandwidth. Setting 15 MHz as the highest frequency to sample, results in a required sampling frequency of 240 MHz. This is a high sampling rate that will produce a significant, even by modern standards, volume of data for real-time beamforming and post-beamforming processing as well as increased power consumption. Therefore, ways to lower that high data throughput are desired.

Maintaining the same sampling clock throughout the whole signal path of the ASDR beamformer from channel sampling to the digitization, yields a number of ways to optimize the power consumption and data. For the portable, battery operated applications, low power mode with sampling clock running at any fraction of main clock rate, set by the user from the device menu may be utilized. Another option is to have a low clock mode for cursory, introductory scanning, and then once the scanning target is found, switch to high clock for the acquisition of diagnostic quality image. Another option would be to acquire lines at the fringes of the image with lower clock and scan lines closer to the center with higher clock.

As it was mentioned above, the ASDR beamformer also allows having separate independent sampling rates for different functional blocks of the beamformer. The focusing delay error minimization requirement needed only at the sample quantization stage in the ASDR beamformer. However, the resultant beamformed analog signal that arrives at the input of the A/D converter falls under the Shannon sampling theorem and can be digitized at much lower sampling rate. Even the summation in the beamformer can be done as low as at Nyquist rate with the proper finely delayed samples from the analog memory. Thus, there may be samples being written into the beamformer memory at WRITE clock rate of 240 MS/s (Mega Samples per second), and the summation operation (READ clock) and subsequent analog-to-digital conversion (DIGITIZE clock) being done, for instance at 60 MS/s, without any loss of the signals content.

Another advantage of having independent clock rates is that the time freed by lowering the adder clock (or READ clock) rate can be used to perform additional beamforming operations. For instance, writing channel samples at 240 MS/s and summing selected samples at 60 MS/s, allows performance of up to four independent beamforming operations (i.e. four subsequent scan lines compounding) on the same channels data volume instead of one using second stage Sample/Hold Cell array as it described and shown on FIG. 11.

Thus, the preferred embodiment has WRITE, READ and DIGITIZE separate and independent sampling clocks for the beamformer analog memory write and read operations, adder circuitry and analog to digital conversion block. Such clocks can be set programmatically to be identical in frequency and phase or have arbitrary phase and frequency difference or have its frequency and phase set as a fraction of the main, sample writing clock. The main clock rate can be lowered to conserve power, lowered dissipated heat or other reasons obvious to skilled in art.

In another embodiment, as the signal propagate in depth and loses its high frequency content, the sampling rate maybe lowered correspondingly for reasons of power conservation or to increase the number of independent beamforming summations done simultaneously or for other reasons obvious to skilled in art.

Figure 15:
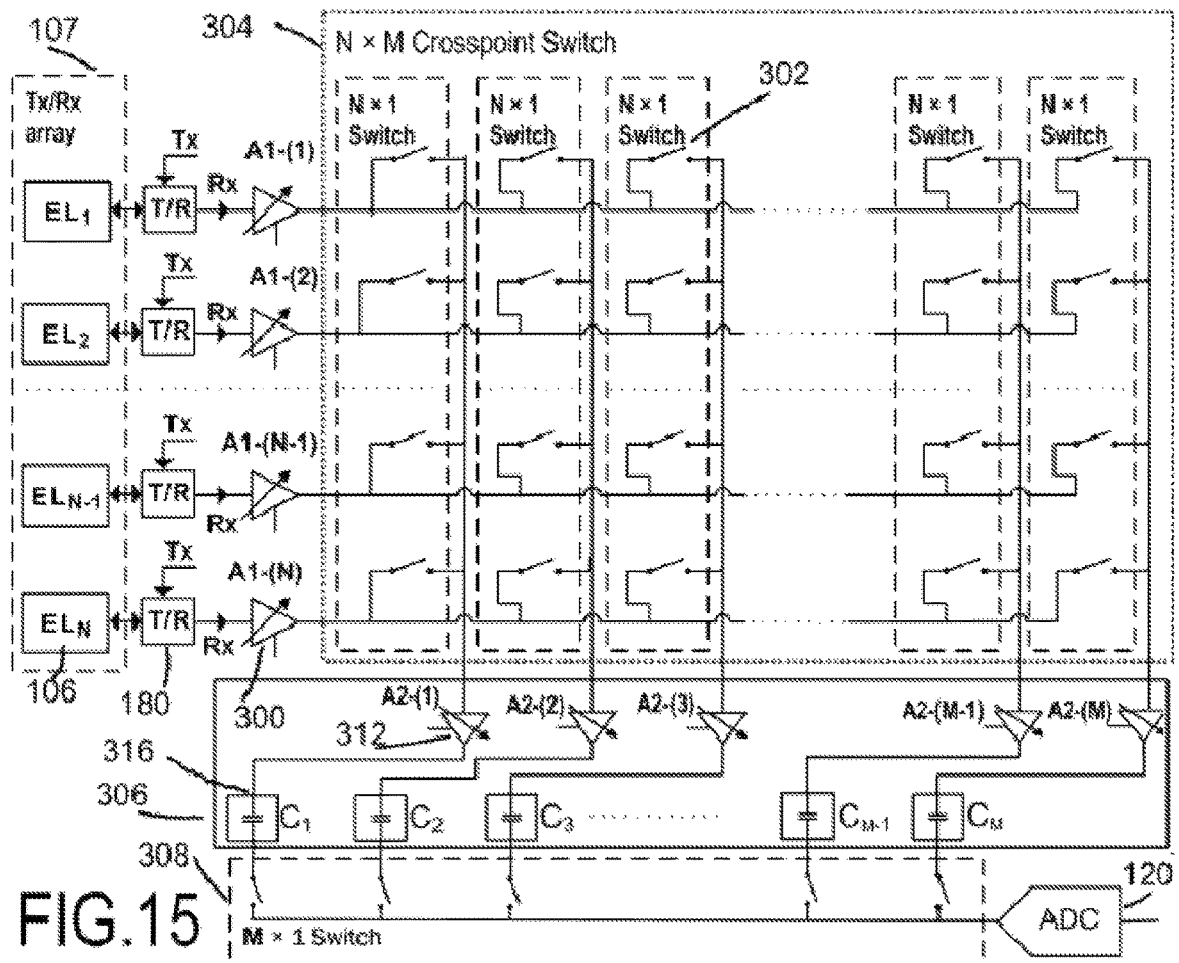
FIG. 15 is an alternative schematic block diagram of receive beamformer channel in accordance with one aspect of the present invention.

ARBITRARY WRITE—SEQUENTIAL READ BEAMFORMER ARCHITECTURE—Referring to FIG. 15, this particular embodiment employs only one row of sample-hold cells 306 and an N×M cross-point switch array 304 that connects N channels of the array 107 to any N selected sample-hold cells out of M number of cells in the ARAM row 306. Another cross-point M×1 switch 308 can connect selected sample-hold cell 316 to the input of the analog-digital converter 120, directly or through an electric amplifier or filter or an integrator if needed. In this embodiment, sample-hold cells 306 sums the time-gated contributions from a plurality of channels and stores the results. The number of SHCs in the memory bank must be larger than a number of sample clock periods needed to fill the maximum desired delay to be corrected by the beamformer. For example, if the maximum delay in signal arrival time to correct will be 1 microsecond and the sampling time will be 40 MegaSamples per second, then M>40 are needed cells to perform the beamforming.

The transmit-receive array 107 is used for generation and the receiving ultrasonic pulses and converting pressure pulses into the other forms of energy, such as electrical, and back. The array 107 can be designed as piezoelectric, MEM's based, magnetostrictive or with any other technology that would allow the transformation of pressure wave information into other forms of energy.

The design of the sample-hold cell 316 can differ from the design of SHC 150, the cell 316 sums the time-gated samples, thus, it works as an integrator circuit. The design of such circuit is a common knowledge, it may be built as a passive RC circuit or as an active, op amp based integrator circuit with additional component being part of the cell 316 itself or being the part of the circuitry outside of the cell.

Similarly to the embodiments described above, the sample-hold cells are organized into the circular or ring buffer, such that when the current sample is written into the last address, the write operation folds and begin writing the next sample at the first address of the array, however in another embodiment, the length of the ARAM memory bank could be sufficient to write the all samples constituting the scan line as (sample rate)×(maximum depth)/(sound speed).

The amplifier blocks 300 and 312 both could contain a filter, a buffer, a voltage controlled amplifier, a voltage follower or any combination of abovementioned circuitry required for signal conditioning task.

Figure 17A:
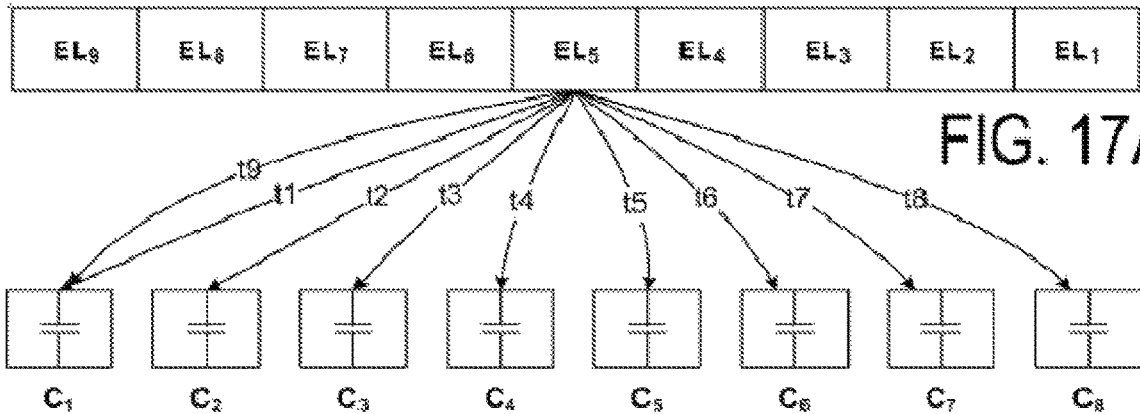
FIGS. 17A, 17B, and 17C schematically illustrates the process of writing to and reading from the SHC array used in the ASDR ultrasonic beamformer of the present invention.
Figure 17B:
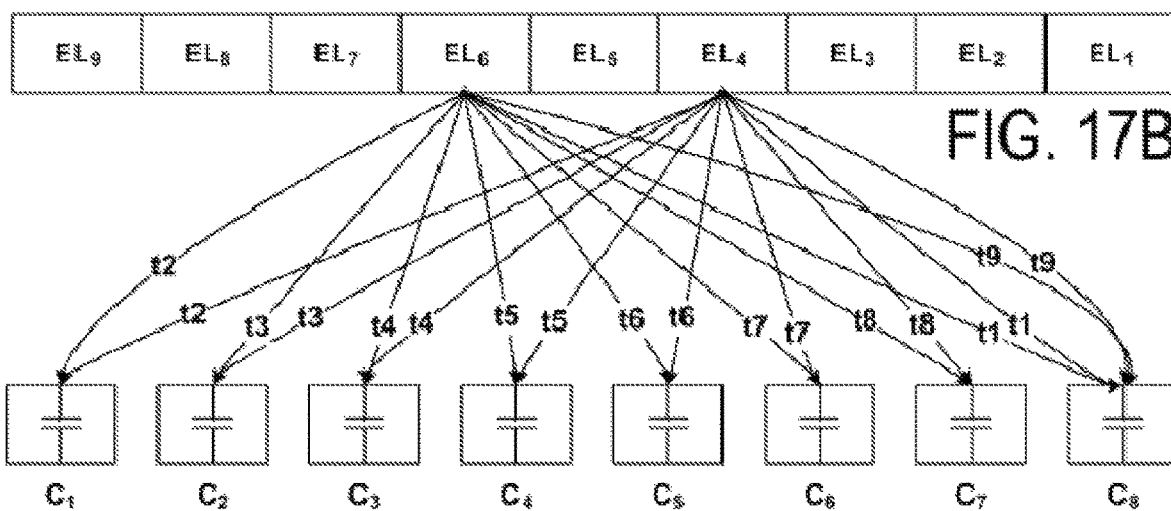
Figure 17C:
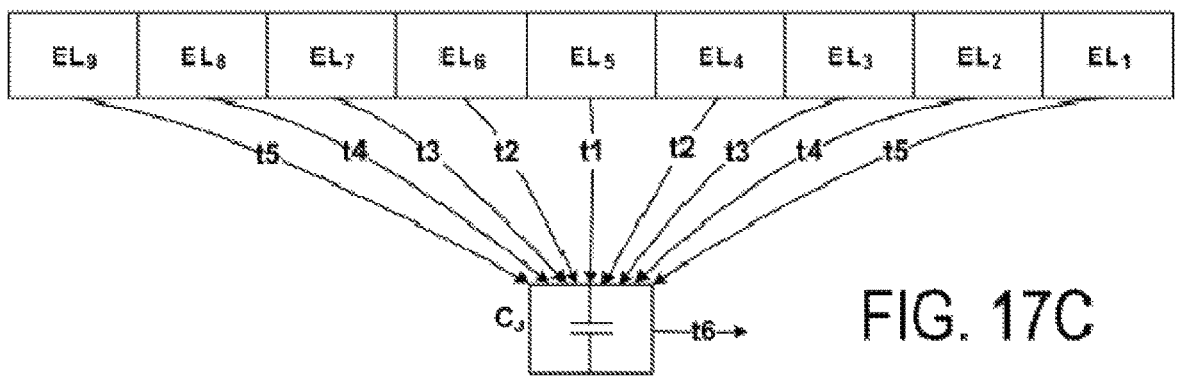

The workings of this embodiment of the receive beamformer can be illustrated by describing the generation of one beamformed RF line in course of ultrasound frame generation. In an oversimplified example, consider a 9 channel aperture 106 with element EL5 being at the center of the aperture having minimum delay and 8 sample-hold cells 316 in ARAM bank 306 and the delays are linear. Then, referring to the FIG. 17A, the central element EL5 will store the analog sample proportional to the received pressure in SH cells C1, C2 . . . C8 with every clock t1, t2, . . . tj as it is shown on FIG. 17A. The elements of aperture EL4 and EL6 will be delayed by the simplified beamforming algorithm by one clock period to correct for the delay in arrival time and store the signal arrived at the time t2 in SH cell C1, thus, adding it to the analog sample from element EL5 already stored there at the previous clock cycle, and then proceed adding samples to cells C2, C3 etc . . . (see FIG. 17B). Referencing one particular cell in the ARAM bank 306, referring to the FIG. 17C, if analog sample from EL5 was stored in the cell in an arbitrary starting time t1, next clock t2 there is adding of samples from EL4 and EL6, then, at t3 there is adding of analog samples from array elements EL3 and EL7 to the content of the cell, then, at t4 there is summing of existing cell content and analog samples from EL2 and EL8, and then at t5 there is adding of the last contribution from the aperture-samples from elements EL1 and EL9. Once finished adding the analog samples from all elements of the aperture participating in the beamforming instance, the system can read the content of the cell in the next clock period t6 and send it to the analog digital converter (directly or through an integrator) or to the next stage of the beamformer.

This beamformer can be used as a stand-alone beamformer of the whole array or be implemented as a sub-aperture beamformer with each sub-beamformer working on a separate ADC or be a part or a stage of a larger multilevel beamformer, working as a first stage sub-aperture beamformer or as an intermediate stage beamformer summing the contributions of previous stages and passing the results to the upper stages or as a last stage beamformer outputting the final RF signal to the analog-digital converter. This beamformer also can work as a beamforming stage in combination with any other existing and future beamformer architectures.

Figure 16A:
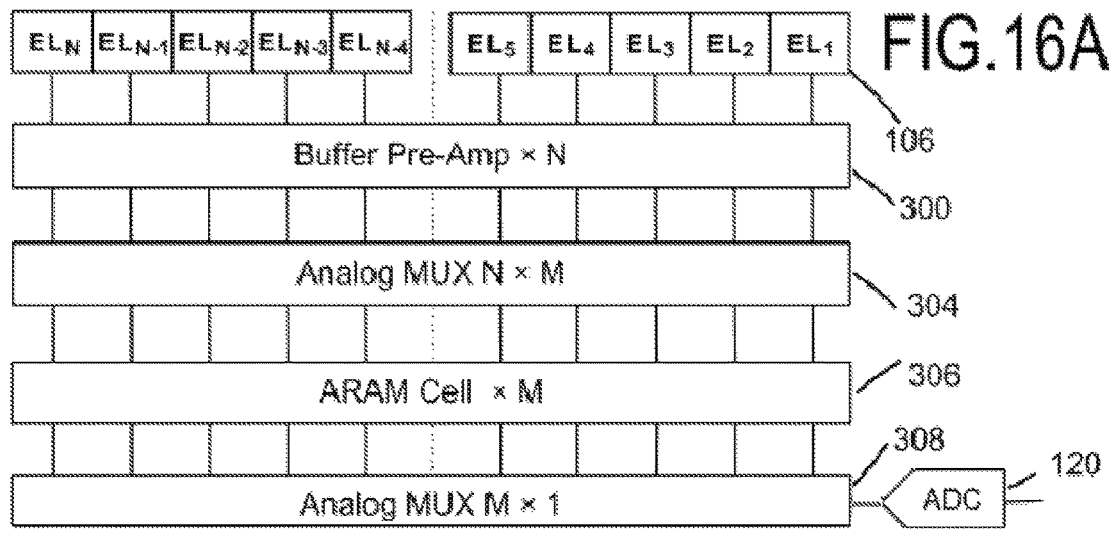
FIGS. 16A, 16B, 16C and 16D are alternative schematic block diagrams of receive beamformer architecture in accordance with four embodiments of the present invention.
Figure 16B:
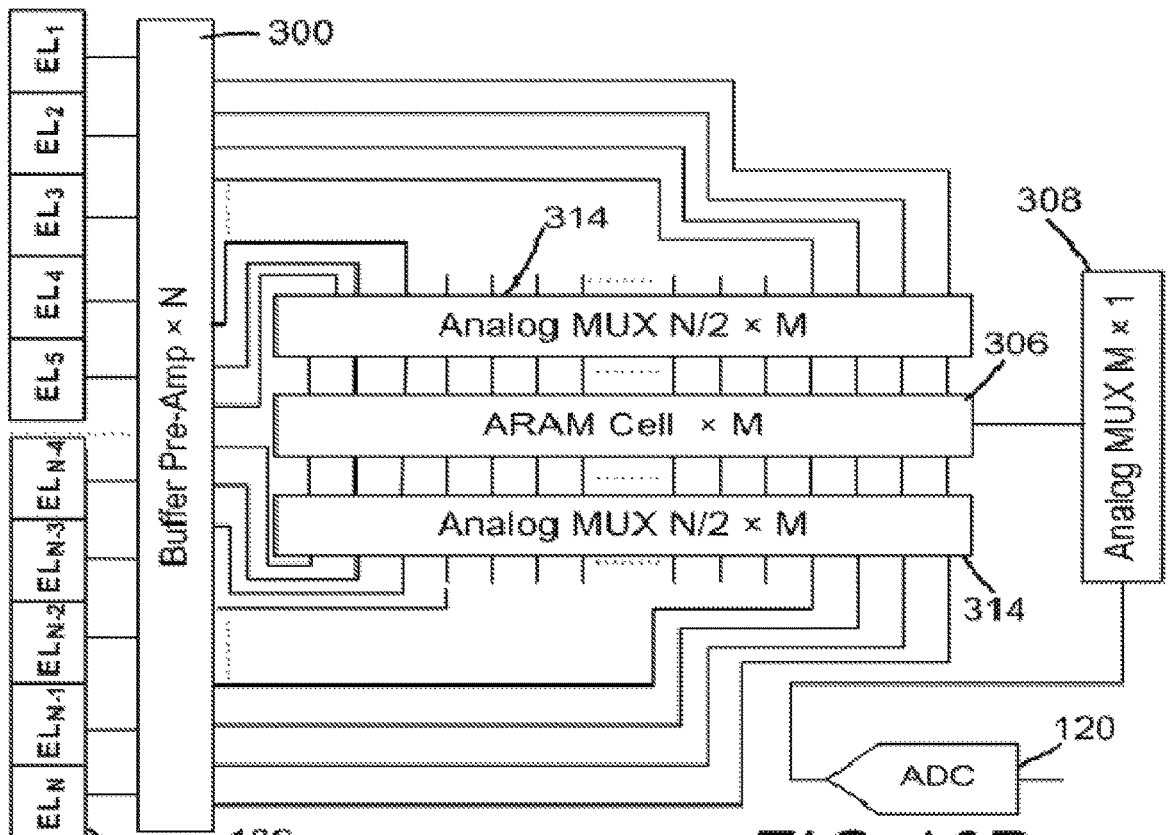
Figure 16C:
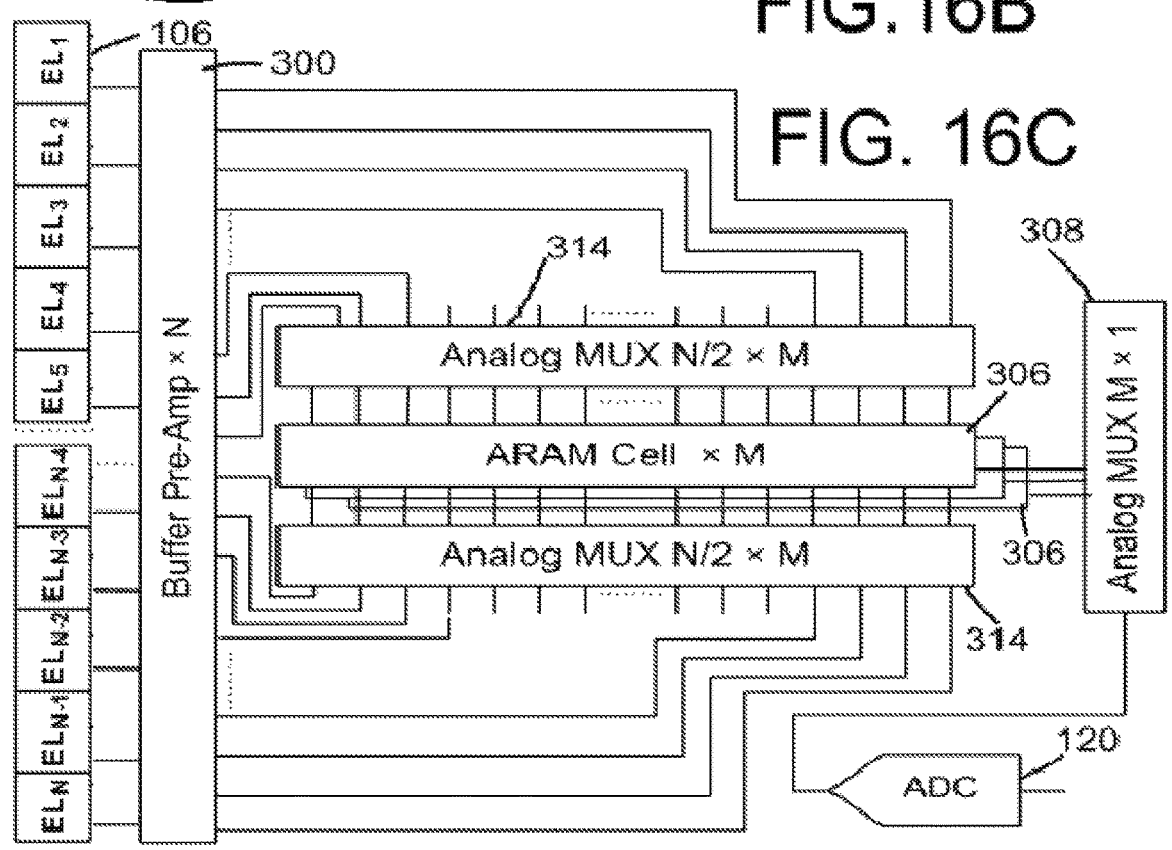

The one row beamformer allows realizing a number of beamforming architectures. Some schematic examples are presented in FIG. 16 with FIG. 16A being the one row beamformer described above in this section, where signals from the array 106 through the signal conditioning circuitry 300 and N×M cross-point switch 304 is being written into the one row ARAM 306 and beamformed signals through the M×1 switch 308 reach the analog to digital converter 120. The cross-point switch 304, for the convenience could be split into at least two sections 314 (FIG. 16B) with independent or a parallel addressing controls. In another embodiment shown in FIG. 16C, instead of one row of sample-hold cells 306 there could be a number of ARAM cell banks each implementing an independent beamforming algorithm. Also in it each ARAM cell may be connected to its own analog to digital converter instead of one ADC common to all ARAM banks 306.

Figure 16D:
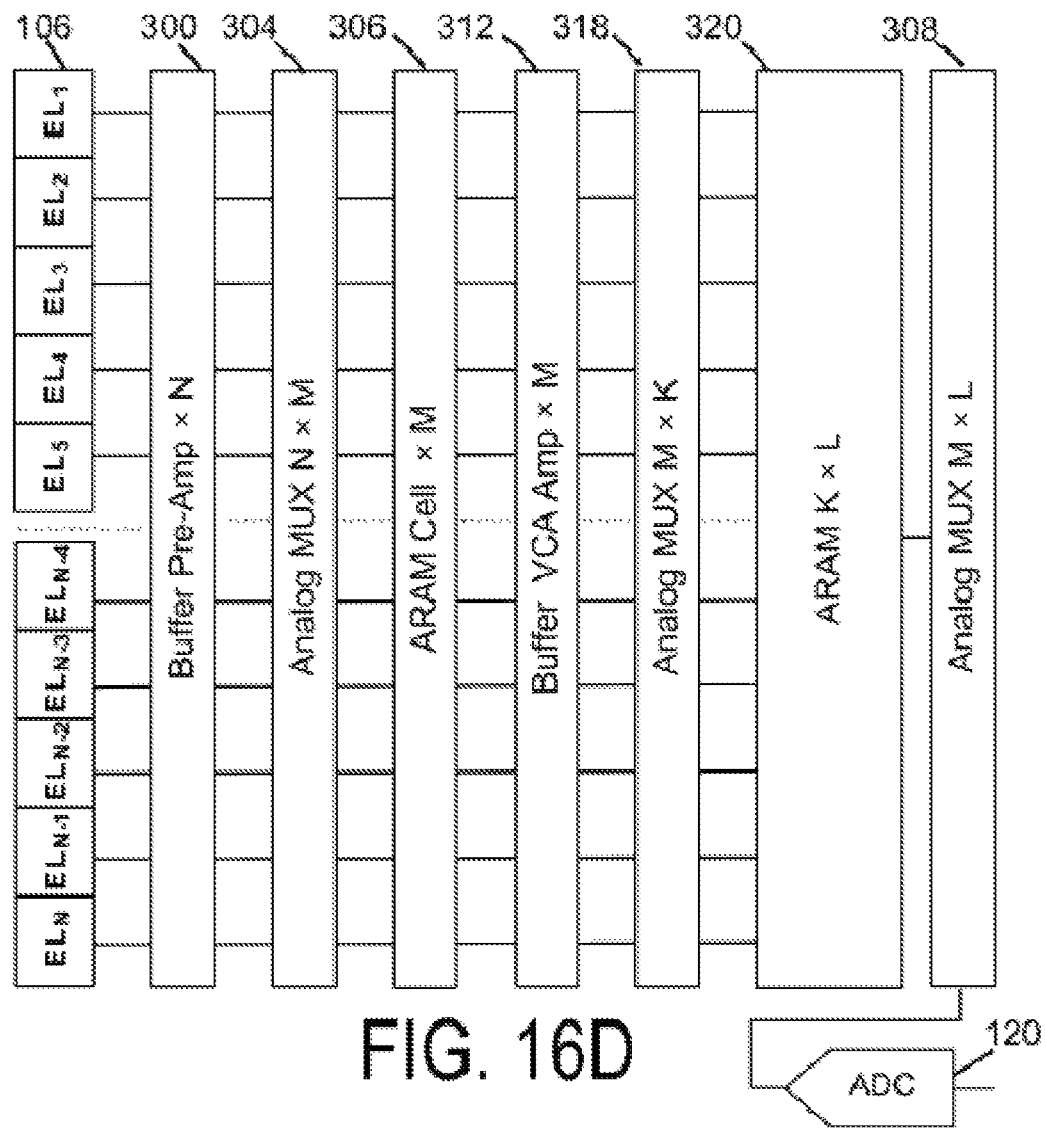

The FIG. 16D shows another embodiment where results of the scan line beamforming in ARAM cells bank 306 instead of digitization are sent into a larger ARAM array 320 that stores the analog samples of all scan lines constituting an image frame for the future extraction and processing, where the number of such sample lines can be smaller, equal or larger than the number of channels. In yet another embodiment, every SH cell in array 320 corresponds to one pixel in the ultrasound diagnostic image to be displayed on the screen. In it, content of the scan line stored in 306 through the conditioning circuitry 312 and cross-point matrix switch 318 is written into the cells of 320 in accordance with scan conversion algorithm.

Figure 18:
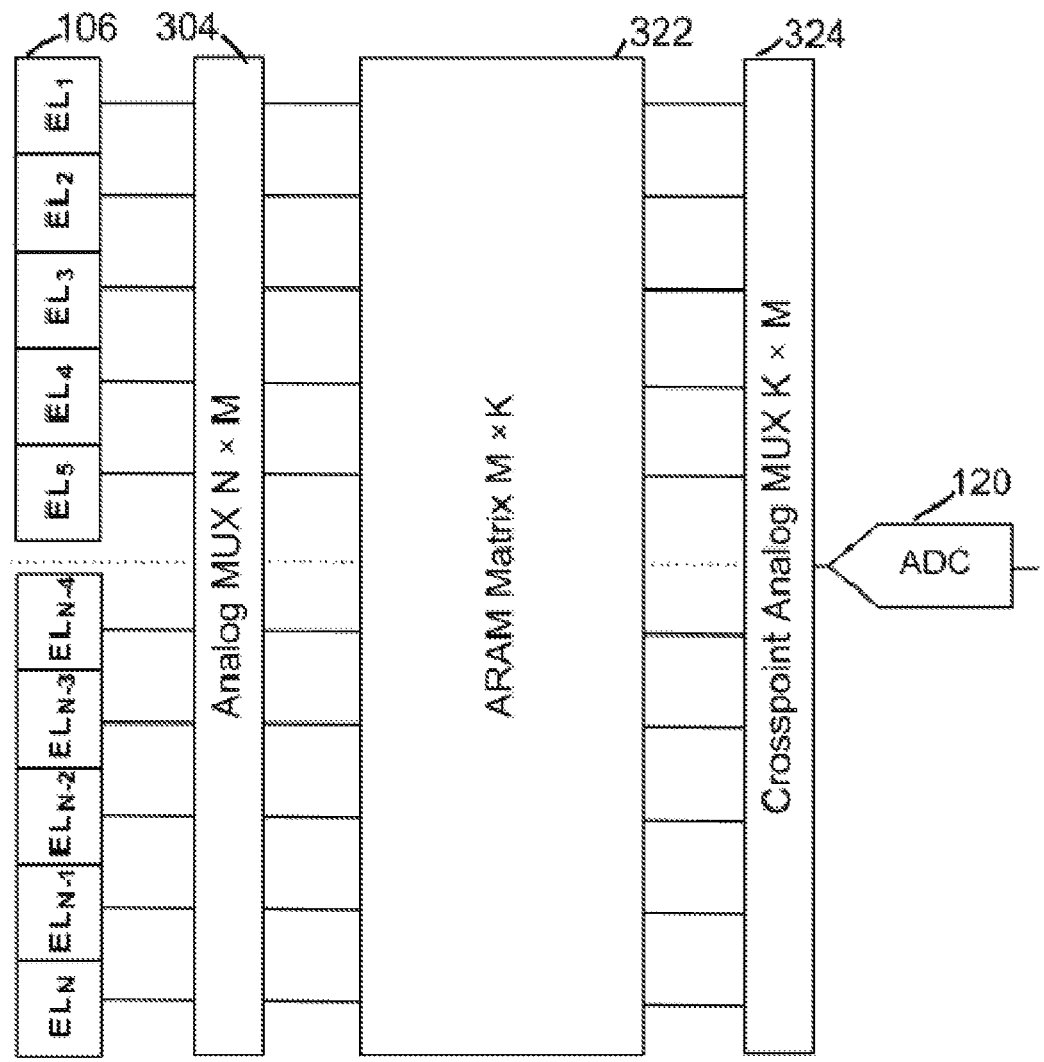
FIG. 18 is a generalized schematic block diagram of receive beamformer architecture in accordance with the present invention.

ARBITRARY WRITE—ARBITRARY READ BEAMFORMER ARCHITECTURE—Another beamformer architecture based on arbitrary write—arbitrary read principle is schematically shown in FIG. 18. In it, each cell of the ARAM 320 represents one sample point or one pixel of an ultrasound frame similar to the embodiment described above in FIG. 16D. At each sample clock period, beamforming algorithm stores the contribution from channels participating in this beamforming instance in the ARAM cell associated with a sample point in the ultrasound image. The number of such sample lines K or rows in the ARAM 320 can be smaller, equal or larger than the number of channels in 106 and the length M of the array 320 can be chosen to accommodate the full depth of ultrasound frame or to accommodate the maximum delay needed to be compensated or be any number of cells between these two number. In this design there could be one AD converter 120 or a number of such AD converters working in parallel, receiving data from the ARAM 320 through the cross-point switch 324. In the embodiment in which each cell of ARAM 320 is associated with one sample point of pre-screen converted or raw RF ultrasound frame, the system stores and sums the contribution from each channel the same way it was described above for the arbitrary write—sequential read beamformer, but the contributions from the channels at each sample clock go not only to the forming the current sampling line but can participate in the beamforming the neighboring sample lines in the frame. In the embodiment in which each cell of the ARAM 320 is associated with one pixel in the ultrasound diagnostic image to be displayed on the screen (so called screen converted image), the beamforming works as described above. The only difference here will be in the sample selection criteria for the current beamforming instance as defined by the beamforming algorithm and the need to have the depth (number of column) of the ARAM 320 to be at least equal to the number of pixels in the frame's scan line.

It is noteworthy that throughout this application is employed simplified diagrams where many significant actual design blocks and components are omitted for the sake of clarity of the representation, however these omissions are apparent to anyone skilled in art and cannot be considered as flaws of the design.

Figure 12:
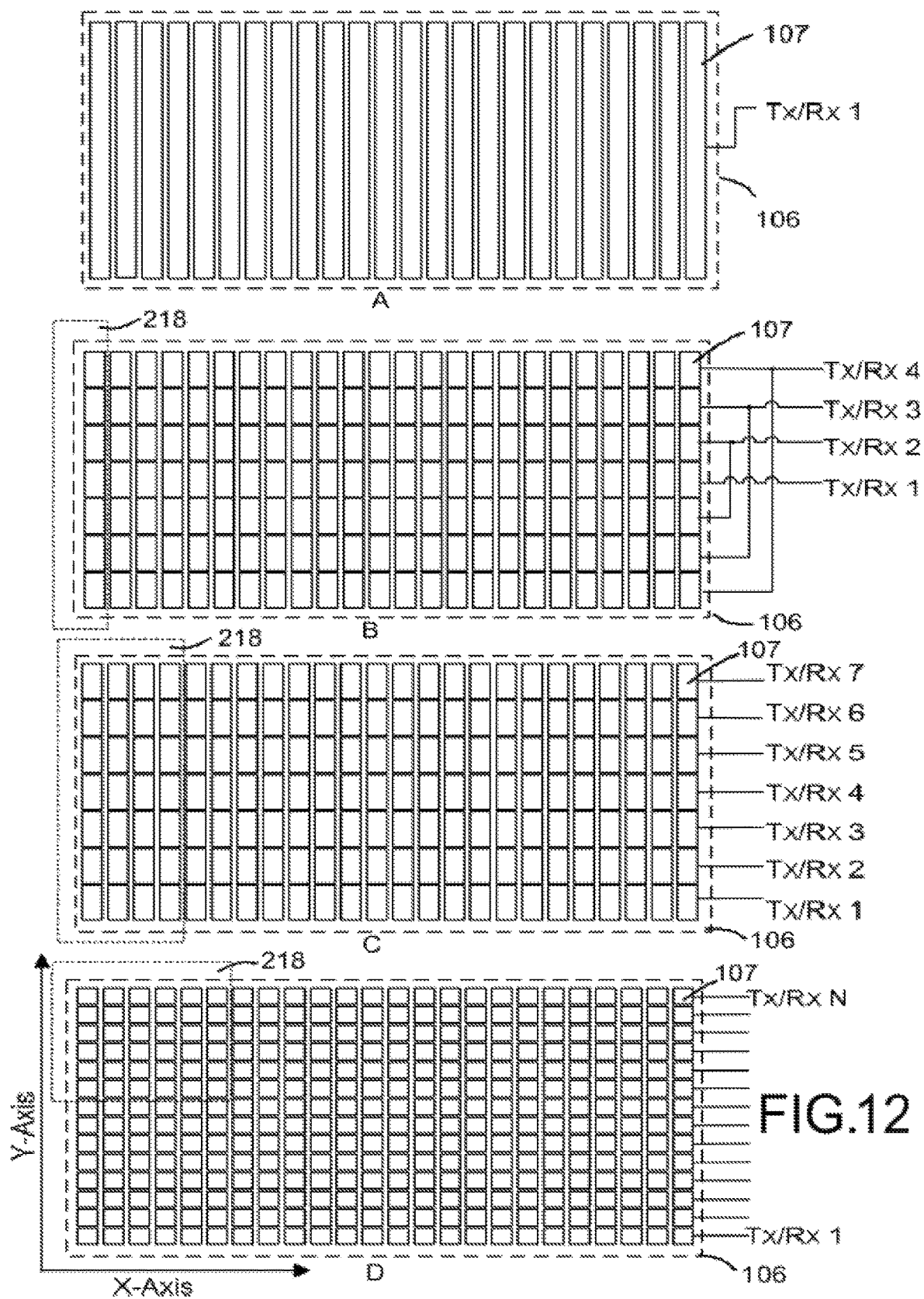
FIG. 12 is a schematic composition of common arrays.

1.5D, 1.75D, 2D ARRAYS OPERATION—The beamforming architectures described above can accommodate any common 1D ultrasound arrays with number of elements (transmit-receive channels) in array going up to a few thousand (refer to FIG. 12A schematically picturing layout of a common 1D array). With a larger element count or with a more complicated structure of the transducer array, being 1.5D, 1.75D, or 2D, this basic architecture can be adapted in the way partially described above (secondary Sample-Hold Cell array). Referring to the top schematic of FIG. 12, the typical 1.5D or 1.75D array is essentially a 1D transducer that has its elements divided in elevation directions with each element preferably having separate beamforming channels. The number of divisions can be any, however when the size of the sub-element in elevation direction (Y-axis on the figure) approaches the size in axial direction (X-axis) and both sizes being equal or less than half of wavelength of the array's central frequency, it is more proper to describe such array as a 2D array (referring to lower schematics of FIG. 12 correspondingly). The main reason for using such an array is that it allows controlling focusing in elevation direction in the same way the axial focusing is controlled, thus, providing constant image slice thickness in elevation with corresponding improvements in contrast and detail resolution.

The main difference between 1.5D and 1.75D arrays is that in 1.5D array elements are connected symmetrically column-wise (referring to FIG. 12) so the elevation focusing is done only in the plane of the image slice or in the Y-Z plane (Z-axis being a depth and directed perpendicular to the FIG. 12 plane) while 1.75D array sub-elements are controlled independently, thus, a limited out-of-plane focusing can be performed, restricted by the grating lobes position. The 2D array, with its elements being close to ½ wavelengths, has the same freedom in focusing in all three directions: elevation, axial, and depth.

Figure 13:
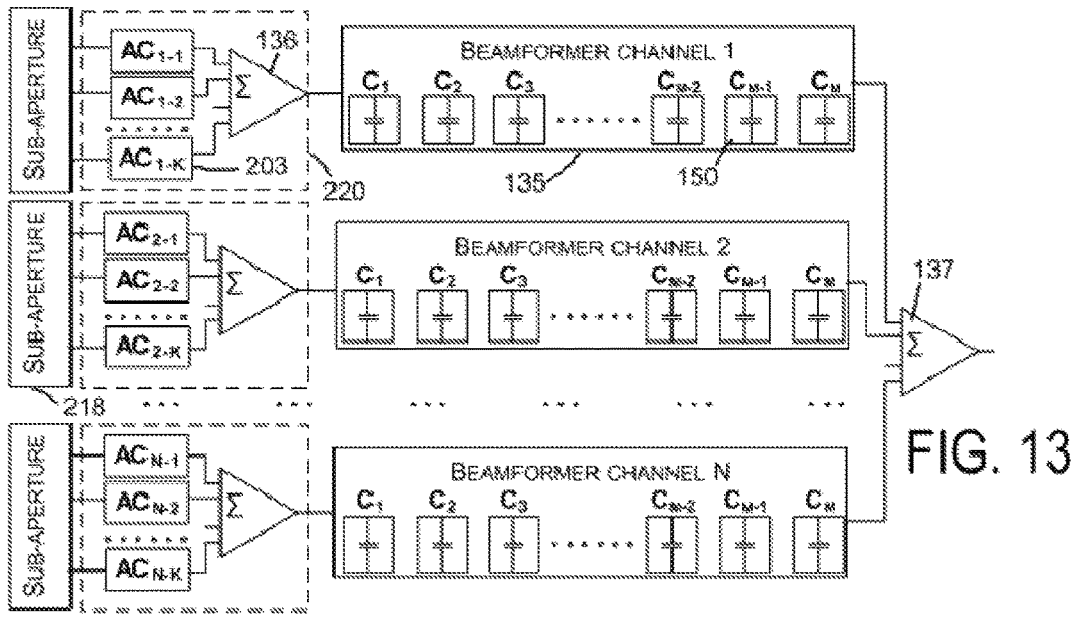
FIG. 13 is a schematic block diagram of sub-aperture transmit and receive beamformer in accordance with one aspect of the present invention.

In the preferred embodiment for 1.5D, 1.75D, and 2D arrays, all elements of the array are divided into groups or sub-apertures 218. Some examples of such sub-apertures are shown on the lower schematics of FIG. 12. The preferred way to select sub-aperture is to assemble an array's elements based on the minimum group delay with respect to the sub-aperture's central element (example on the lowest schematic of FIG. 12) allowing a small number of sample-hold cells in the receive beamformer channel 132 of primary analog channel 203 (FIG. 13), where under the primary (or first) analog channel it is understood the channel is connected to the array element. The elements of sub-aperture 218 connect to analog channel 203 (with smaller number of SHC 150) then the content of cells 150 from different channels within sub-aperture is beamformed in the way described above and the output of summing circuit 136 is connected to the second stage beamformer channel 135 which has the same design as beamformer channel 132, but numbered differently to show that first and second stage beamformer channels 132 and 135 are physically different devices that might have different internal structure (e.g. number of cells 150). The contribution of 135 is summed by the second stage summing circuit 137. The output of 137 is the beamformed analog signal put to the input of analog digital converter 120 to create a digitized beamformed RF signal. It is understood that this invention allows for any number of sub-apertures to be formed. It is also understood that this invention allows for any number of beamforming stages to be implemented, where each collected contribution of lower level sub-apertures become a single channel in the next level sub-aperture until a single beamformed signal is outputted.

In one embodiment for 1.5D, 1.75D, and 2D arrays, all beamforming is done in the ASDR beamformer hardware placed next to the array. In another embodiment, some sub-aperture beamforming could be done in ASDR beamformer next to the array, and then partially beamformed signals are sent via wire or wireless link to the ultrasound machine hardware where the final beamforming is done in ASDR beamformer or in the prior art digital beamformer. The main advantage of such approach is the reduction in number of cables running from the probe to the ultrasound hardware.

Figure 14:
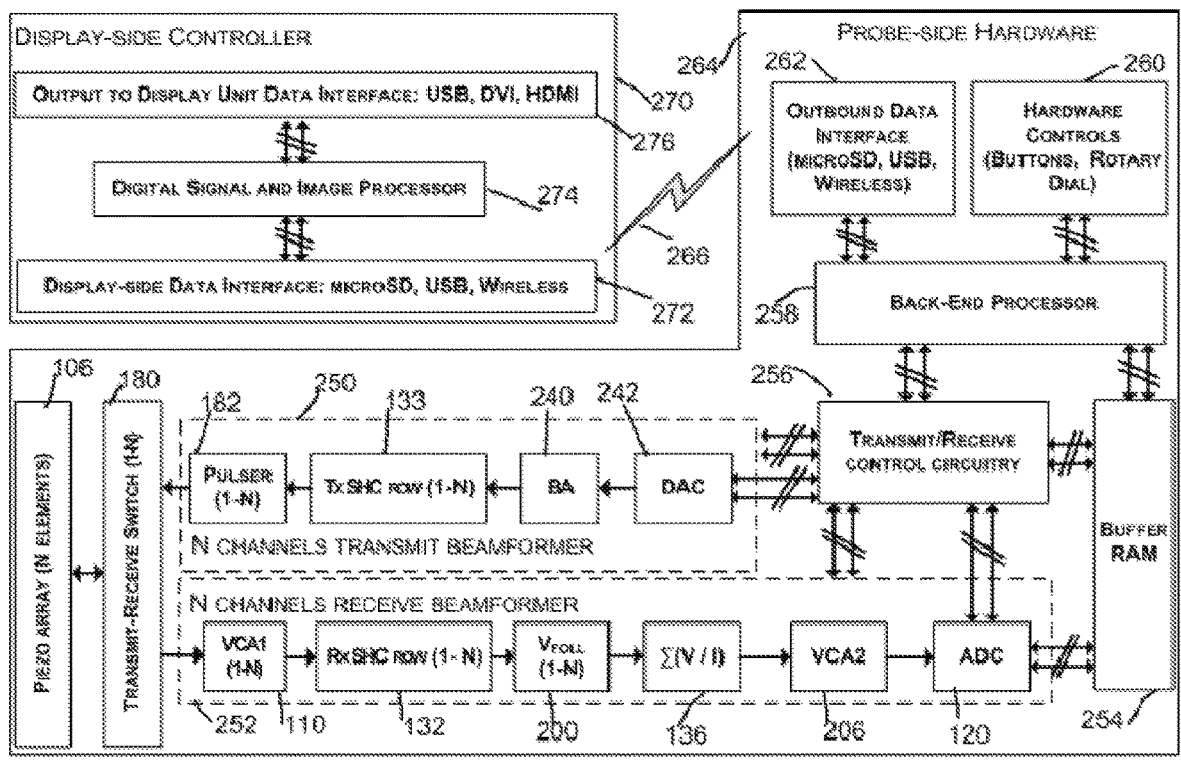
FIG. 14 is a schematic block diagram of an ASDR ultrasound system in accordance with the present invention.

PORTABLE ULTRASOUND DEVICE AND ASIC STRUCTURE—The ASDR beamformer described in this invention can be used to build compact ultrasound diagnostic devices that combine small size and power consumption with high image quality that results from the high channel count of full aperture and short signal path 109. Such system can be implemented as system-on-the-probe where all hardware necessary for signal acquisition and processing fits in the transducer array handle together with the battery, which wirelessly transmits beamformed and processed signals to the receiver that is connected to a display unit such as a laptop, smartphone, tablet, or a TV set where images are displayed. In one embodiment of such a diagnostic ultrasound system, as it is shown on the example of schematic diagram on FIG. 14, the ASDR beamformer is implemented as one or few integral chips (ICs) that are placed in immediate vicinity of the transducer array 106.

Functioning of the N channels (equal to the number of elements) receive beamformer 252 was described above. In it, the signal from each element of array 106 through T/R switch 180 goes to VCA 110, S/H cells bank 132, then the voltage level of the selected SHC elements through the follower 200 go to the input of summing circuit 136 and via VCA 206 go to the input of ADC 120. The digitized data from the output ADC are written in buffer memory 254.

The transmit-receive control circuitry block 256 controls the flow of data and command in and out of receive beamformers 250, 252, buffer memory 254, and back-end processor 258. The transmit beamformer 250 writes voltage levels from digital-to-analog converter 242 via buffer amplifier 240 to the transmit SHC array 133. The voltage level samples from 133 are sequentially sent to the puller 182 to form the high voltage pulse that is sent to the transducer array. The transmit beamforming delays are controlled by the T/R control circuitry block 256. The transmit beamformer DAC 242 may refresh the content of array SHC 133 while the Rx beamformer is in receive mode. The back-end processor 258 performs initial signal and image processing on raw RF data received from the buffer memory including, but not limited to, data flow organization (such as creation of line and frame headers), filtering, I/Q, B-mode conversion, Doppler data extraction, data compression, scan image forming, and other typical tasks of the back-end DSP. It also receives and interprets the commands from any buttons and rotary dial controls of the ultrasonic hardware control block 260. Another task of the processor 258 is to organize the flow of information to the outside storage and processing interface block 262, that controls writing ultrasound data to the non-volatile memory storage (such as flash card, SD or a micro-SD), wire based data transfer (such as USB) port and wireless data interface.

The scan data (such as raw RF, Doppler, B-mode, image, volume data) are transferred outside from the probe-side hardware block 264 via wire link or wireless link 266 to the display-side hardware block 270. There, data decoded by the interface 272, the image processed in the block 274 to fit the format of the current display device and outputted to the display interface 276 that transmits the data in the format accepted by the display device through USB, HDMI, DVI, or another input signal port.

In one embodiment of such a system, the ASDR beamformer is built on one ASIC that along with the analog front-end, SHC arrays, digital back end, and control circuitry may include all functional blocks described in block 264 with the exception of the transducer array. In another embodiment, some of the functional blocks or parts of such blocks described in block 264 may be realized separately from the ASDR ASIC. In another embodiment, the system may consist not from a single ASDR ASIC but from a few independent ASDR beamformers working on the single ADC (or each on their own ADC) where each ASDR beamformer has a part of the array 106 as its sub-aperture and final beamforming is done digitally on data streams coming from the multitude of ASDR beamformers. In yet another embodiment few independent ASDR beamformers can be working on the same array 106 with time interleave to achieve higher sampling rates. In one embodiment of such a system, the display side controller 270 is implemented as a dongle that connects to the display device via standard data connection like USB or HDMI and interact with the probe-side hardware 264 wirelessly. In another embodiment, there is control and image processing software loaded into the display unit that allows control of the probe-side hardware 264 via dongle 270.

In one embodiment of such a system, the controller 270 can be attached to the probe connector of any diagnostic ultrasound device as an after-market add-on. It would wirelessly receive the ultrasound data from the probe-side hardware and transmit it into the ultrasound device replacing the existing corded 1D probe. Simple measures can be taken to ensure the preservation of high dynamic range and the resolution of the ASDR system. For example, the incoming beamformed RF signal could be routed through one channel of the digital beamformer with analog front end electronics tuned for the minimum noise settings and then being restored and digitized, or the incoming beamformed RF signal could be routed through all beamformer channels in parallel and then summed with zero delay, or incoming RF signal could be routed through the host system's analog front end and the digital beamformer in its digital form, for instance, by assigning 16 beamformer channels each to carry one logical level of 16 bit data of the incoming RF signal, or by other means obvious to anyone skilled in art. The control of the scanning process, commands and scan parameters in such an embodiment also can be done either through the data transfer from the host device to the ASDR device via dongle 270. Such embodiment would also include a charging station for the ASDR probes being a part of the host machine as well as battery health and array health indicators.

In one embodiment of such a diagnostic ultrasound system, an accelerometer a gyroscope and software algorithms are added to the system to allow recording precise 3D spatial positions of all the scan lines and frames taken in the course of ultrasonic examination. In this embodiment no scan line or a frame are discarded in course of an exam but stored in the memory. Furthermore, each scan line and frame can participate in the creation of the current frame on the screen if they contain data previously recorder in that position. Thus, in course of the examination, when the operator move the probe a 3D volume is reconstructed with density of data greater in the locations and directions where ultrasound probe spend more time. One of the advantage of this scheme is that operator may conduct a rough sweep over the wider area (like a "painting" the body area) and concentrate most of its scanning time in the region of interest. The large sweep will give him a general appreciation of the surrounding anatomy while focused scan will generate better images that a single frame.

It should be noted that the beamformer system is implemented partially in hardware, partially in firmware and partially in software such that precise boundaries between these parts can be established by the needs of the implementation. Further, in all descriptions and schematic diagrams the placement of elements or blocks such as VCA, LNA, voltage followers switches, etc. that are secondary to the understanding of the invention are not strictly followed, assuming that anybody with ordinary knowledge of electronic design would understand their functions would determine where they should be placed in the actual working schematics, their structure, and parameters.

The above description describes an Analog Store Digital Read ultrasound beamforming method for an ultrasound imaging system comprising the steps of: i) Providing an ultrasonic array formed of individual ultrasonic array elements configured for transmission and receiving; ii) Dividing the individual array elements into individual channels, wherein each channel comprises at least one array element; iii) Creating a receiving input signal for each channel from inputs received from each array element of the channel; iv) Sampling each receiving input signal for each channel at a sampling rate and storing the sampled data in a bank of sample-hold cells which are associated with that channel, wherein the bank of sample-hold cells form an analog random access memory for the sampled receiving input signal; v) Selecting at least one sample-hold cell data from at least one channel for each particular output time for each beamforming instance in accordance with a beamforming algorithm; vi) Summing all of the selected sample-hold cell data from the associated channels for the beamforming instance forming an analog beamformed received signal sample for the beamforming instance; and vii) Digitizing the analog beamformed received signal sample.

CONCLUSION—As discussed above the individual channels will generally include, not just the array elements but also the control electronics. Further it is important to note the sampling rate may be fixed or may be variable and may further be independent of the rate the data is read from the cells or the rate such is digitized. The digitized sample is typically stored for further processing as known in the art. In the Analog Store Digital Read ultrasound beamforming method for an ultrasound imaging system, each channel may comprise only one array element. Further, the creating a receiving input signal for each channel may include processing the inputs from the array elements through at least one voltage controlled amplifier and at least one filter. Additionally, each channel may use less than 40 milliwatts in operation, generally less than 25 milliwatts per channel and typically about 10 milliwatts per channel or even less. Each sample-hold cell may be formed as a capacitor based element. It is noteworthy that selected sample-hold data pass through an analog filter or/and amplifier with variable gain with purpose to assign proper Time Gain Compensation (TGC) values, aperture selection and apodisation weighting before the summing for proper signal to noise attenuation.

In the Analog Store Digital Read ultrasound beamforming method the number of sample-hold cells in each bank may be equal to or greater than the sample rate per second times the maximum desired delay for the signal path. Further, a sampling speed for the storing of the sampled data in the bank of sample-hold cells may be independent of a sampling speed for reading the sampled data in the bank of sample-hold cells.

The Analog Store Digital Read ultrasound beamforming method may further include the step of storing at least one shape of a transmission output pulse signal for each transmission channel in a bank of transmission sample-hold cells which are associated with that transmission channel. In one embodiment a single bank of transmission sample-hold cells are associated with multiple transmission channels. Further the method may provide that the same bank of sample-hold cells forms the receiving bank of sample-hold cells and the bank of transmission sample-hold cells for each channel. Alternatively, each channel may be associated with one receiving bank of sample-hold cells and one distinct bank of transmission sample-hold cells.

The Analog Store Digital Read ultrasound beamforming method for an ultrasound imaging system as described above provides that multiple beamforming instances associated with multiple algorithms may be utilized, and may further include the step of storing each of the analog beamformed received signal for each beamforming instances in a bank of beamform sample-hold cells prior to digitizing the analog beamformed received signals.

As summarized above, there are two ways to organize sample memory: 1) During the operation the data are written continuously into the ARAM organized as a ring buffer, such that when the current sample is written into the last address, the write operation folds and begin writing at the first address of the array; or 2) The ARAM memory depth is sufficient to store the whole length of the channel data for the scan line (here the maximum delay is the time required for the signal to travel to the maximum desired scan depth and back to the receiver) providing greater freedom for multiple beamforming.

The above description defines the transmit beamforming essentially the same way as it describes the receive beamforming. In short a transmit beamformer that forms an ultrasonic pulse by sequentially reading analog sample values stored in transmission bank of sample-hold cells in channels selected by the beamforming algorithm, sending them to the high voltage amplifier or generator connected to the elements of the transmit-receive array where each channel begin to read analog sample values with predefined time delays and sampling rates in accordance to the transmit beamforming algorithms.

The above description sets forth an Analog Store Digital Read ultrasound beamformer for an ultrasound imaging system comprising: i) An ultrasonic array formed of individual ultrasonic array elements configured for transmission and receiving, wherein the individual array elements are grouped into individual channels, wherein each channel comprises at least one array element; ii) A Receiving input signal control circuitry for creating receiving input signals for each channel from inputs received from each array element of the channel; iii) A plurality of banks of sample-hold cells with each bank of sample-hold cells associated with one channel, wherein the beamformer is configured for sampling each receiving input signal for each channel at a sampling rate and storing the sampled data in one bank of sample-hold cells which are associated with that channel, wherein the bank of sample-hold cells form an analog random access memory for the associated sampled receiving input signal; iv) A beamforming processor configured for selecting at least one sample-hold cell data from at least one channel for each beamforming instance in accordance with a beamforming algorithm; v) An analog summation element for summing all of the selected sample-hold cell data from each channel for each beamforming instance and forming an analog beamformed received signal for the beamforming instance; and vi) An Analog-to-Digital converter for digitizing the analog beamformed received signal.

At least the beamforming processor may be formed as an integrated circuit. Essentially the circuitry implementing the beamforming method may comprise an integrated circuit (IC) such as an application-specific integrated circuit (ASIC).

The above description also defines an Analog Store Digital Read ultrasound beamforming system for an ultrasound imaging system comprising an ultrasonic array formed of individual ultrasonic array elements configured for transmission and receiving, wherein the individual array elements are formed into individual channels, wherein each channel comprises at least one array element and each channel uses less than 40 milliwatts in operation, and generally less than about 25 milliwatts per channel, often less than 15 milliwatts per channel or even less than 10 milliwatts per channel.

The compact ultrasound imaging system formed according to the present invention may send the beamformed signal to an outside display device wirelessly or wired in a display neutral system or manner. The system described provides a compact ASIC, low power device and high channel count (128 or more), with simple scalable architecture. It should be apparent that the beamformer system is implemented partially in hardware, partially in firmware and partially in software such that precise boundaries between these parts can be established by the needs of the implementation.

Further regarding, Sub-aperture beamforming and the secondary Sample-Hold cell bank described above, first, second and tertiary levels (any number of beamforming stages) of sub-aperture beamforming using ARAM beamforming may be provided. An effective way to select sub-aperture is to assemble an array's elements based on the minimum group delay with respect to the sub-aperture's central element. The system may be mix of beamformer methods ARAM, analog, digital for different stages of sub-aperture beamformer. Further the stages of beamforming can be spatially separated, such as a first stage on the probe and a second on the hardware side.

One advantage of the invention is that it provides significant reduction in the size of the diagnostic ultrasound imaging system such that the hardware build upon ASDR ultrasound beamformer architecture can be placed in one or few application specific integrated chips (ASIC) positioned next to the ultrasound array and the whole diagnostic ultrasound imaging system could fit in the handle of the ultrasonic probe while preserving most of the functionality of a cart-based system. Another advantage of the invention is that such compact system allows sending data and diagnostic images wirelessly to any image display equipped to receive such transmissions or having such a receiver attached to data ports such as USB or FireWire of the display unit. Another advantage of the invention is that it provides an improved signal-to-noise ratio by drastic reduction in hardware complexity of the signal path from the transducer elements to the digitizer. Such a shortening of the signal path is achieved by making redundant a number of components of the signal path such as analog high voltage and channel multiplexors, signal cable, and connectors used in prior art to connect ultrasound array with signal processing hardware.

Another advantage of the invention is that it further improves the signal-to-noise ratio, and diagnostic image contrast, and spatial resolution by implementing the full aperture beam formation in which every element of the array operates its' own transmit and receive channel (128 parallel transmit-receive channels for a typical 128 elements 1D array) and thus, the available aperture is equal to the size of the whole array. Another advantage of the invention is that it uses lower power per channel, thus, allowing for extended time operation on battery power. Another advantage of the invention is that implementation in one or few ASICs significantly reduce the cost of production of ultrasound system. Another advantage of the invention is that it has scalable architecture enabling the construction of ultrasound arrays with any number of elements by linear expansion (e.g. one ASIC controls 128 element 1D array, two ASIC—256 elements array, and so on). Another advantage of the invention is that it improves image quality and reduces the cost of systems built with 1.5D, 1.75D and 2D arrays.

Although the present invention has been described with particularity herein, the scope of the present invention is not limited to the specific embodiments disclosed. It will be apparent to those of ordinary skill in the art that various modifications may be made to the present invention without departing from the spirit and scope thereof. For example the array may be selected in length to provide a whole-scan-line channel storage option, which would not change the fundamentals of operation of the system or method of the invention.

What is claimed is:

1. An Analog Store Digital Read ultrasound beamforming method for an ultrasound imaging system comprising the steps of:
   providing an ultrasonic array formed of individual ultrasonic array elements configured for transmission and receiving;
   dividing the individual array elements into individual channels, wherein each channel comprises at least one array element;
   creating a receiving input signal for each channel from inputs received from each array element of the channel;
   sampling each receiving input signal for each channel at a sampling rate and storing the sampled data in a bank of sample-hold cells which are associated with that channel, wherein the bank of sample-hold cells form an analog random access memory for the sampled receiving input signal;
   selecting at least one sample-hold cell data from at least one channel for each particular output time for each beamforming instance in accordance with a beamforming algorithm;
   summing all of the selected sample-hold cell data from the associated channels for each respective beamforming instance forming an analog beamformed received signal sample for each respective beamforming instance; and
   digitizing the analog beamformed received signal sample, and wherein the number of sample-hold cells in each bank is equal to or greater than the sample rate per second times the maximum desired delay for the signal path, and wherein a sampling speed for the storing of the sampled data in the bank of sample-hold cells is independent of a sampling speed for reading the sampled data in the bank of sample-hold cells.

2. A Analog Store Digital Read ultrasound beamforming method for an ultrasound imaging system comprising the steps of:
   providing an ultrasonic array formed of individual ultrasonic array elements configured for transmission and receiving;
   dividing the individual array elements into individual channels, wherein each channel comprises at least one array element;
   creating a receiving input signal for each channel from inputs received from each array element of the channel;
   sampling each receiving input signal for each channel at a sampling rate and storing the sampled data in a bank of sample-hold cells which are associated with that channel, wherein the bank of sample-hold cells form an analog random access memory for the sampled receiving input signal;

selecting at least one sample-hold cell data from at least one channel for each particular output time for each beamforming instance in accordance with a beamforming algorithm;

summing all of the selected sample-hold cell data from the associated channels for each respective beamforming instance forming an analog beamformed received signal sample for each respective beamforming instance; and digitizing the analog beamformed received signal sample, and wherein multiple beamforming instances associated with multiple algorithms are utilized, and further including the step of storing each of the analog beamformed received signal for each beamforming instances in a bank of beamform sample-hold cells prior to digitizing the analog beamformed received signals.

3. An Analog Store Digital Read ultrasound beamformer for an ultrasound imaging system comprising:

an ultrasonic array formed of individual ultrasonic array elements configured for transmission and receiving, wherein the individual array elements are grouped into individual channels, wherein each channel comprises at least one array element;

a receiving input signal control circuitry for creating receiving input signals for each channel from inputs received from each array element of the channel;

a plurality of banks of sample-hold cells with each bank of sample-hold cells associated with one channel, wherein the beamformer is configured for sampling each receiving input signal for each channel at a sampling rate and storing the sampled data in one bank of sample-hold cells which are associated with that channel, wherein the bank of sample-hold cells form an analog random access memory for the associated sampled receiving input signal;

a beamforming processor configured for selecting at least one sample-hold cell data from at least one channel for each beamforming instance in accordance with a beamforming algorithm;

an analog summation element for summing all of the selected sample-hold cell data from each channel for each beamforming instance and forming an analog beamformed received signal for each beamforming instance; and an Analog-to-Digital converter for digitizing the analog beamformed received signal, and wherein multiple beamforming instances associated with multiple beamforming algorithms are utilized, and further including a bank of beamform sample-hold cells configured for storing each of the analog beamformed received signal for each given beamform prior to digitizing the analog beamformed received signal.

4. The Analog Store Digital Read ultrasound beamformer for an ultrasound imaging system according to claim 3 wherein each channel comprises only one array element, and wherein each channel uses less than 40 milliwatts in operation.

5. The Analog Store Digital Read ultrasound beamformer for an ultrasound imaging system according to claim 3 wherein each sample-hold cell is formed as a capacitor based element and wherein at least the beamforming processor is formed as an integrated circuit.

6. The Analog Store Digital Read ultrasound beamformer for an ultrasound imaging system according to claim 3 wherein the number of sample-hold cells in each bank is equal to or greater than the sample rate times the maximum desired delay for the signal path.

7. The Analog Store Digital Read ultrasound beamformer for an ultrasound imaging system according to claim 3 further including a transmission beamformer for storing at least portions of a transmission output pulse signal in a bank of transmission sample-hold cells which are associated with that channel.

8. The Analog Store Digital Read ultrasound beamformer for an ultrasound imaging system according to claim 7 wherein a single bank of transmission sample-hold cells are associated with multiple channels.

9. The Analog Store Digital Read ultrasound beamformer for an ultrasound imaging system according to claim 7 wherein the same bank of sample-hold cells forms the receiving bank of sample-hold cells and the bank of transmission sample-hold cells for at least one channel.

10. The Analog Store Digital Read ultrasound beamformer for an ultrasound imaging system according to claim 7 wherein each channel is associated with one receiving bank of sample-hold cells and one distinct bank of transmission sample-hold cells.

* * * * *